(12) United States Patent
Murray et al.

(10) Patent No.: US 12,171,992 B2
(45) Date of Patent: Dec. 24, 2024

(54) TAMPER EVIDENT CAP WITH RFID FOR SYRINGES

(71) Applicant: Fresenius Kabi USA, LLC, Lake Zurich, IL (US)

(72) Inventors: Christopher J. Murray, Chicago, IL (US); Anthony Ferraro, Vernon Hills, IL (US); Gang Ju, Vernon Hills, IL (US); Robert Speek, Highland Park, IL (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 771 days.

(21) Appl. No.: 17/235,909

(22) Filed: Apr. 20, 2021

(65) Prior Publication Data

US 2021/0236744 A1 Aug. 5, 2021

Related U.S. Application Data

(63) Continuation-in-part of application No. 16/850,396, filed on Apr. 16, 2020, now Pat. No. 11,964,142, (Continued)

(51) Int. Cl.
*A61M 5/50* (2006.01)
*A61J 1/20* (2006.01)
(Continued)

(52) U.S. Cl.
CPC .......... *A61M 5/5086* (2013.01); *A61J 1/2096* (2013.01); *A61M 5/3134* (2013.01);
(Continued)

(58) Field of Classification Search
CPC .............. A61M 5/5086; A61M 5/3134; A61M 5/3202; A61M 2005/3104;
(Continued)

(56) References Cited

U.S. PATENT DOCUMENTS 4,174,238 A 11/1979 Fowles et al.
4,639,250 A * 1/1987 Rycroft ................. A61M 5/346
604/206
(Continued)

FOREIGN PATENT DOCUMENTS

EP 0716860 A2 6/1996
EP 0766975 A1 4/1997
(Continued)

OTHER PUBLICATIONS

International Patent Application No. PCT/US2019/063283; Inl'l Search Report and the Written Opinion; dated Apr. 2, 2020; 28 pages.
(Continued)

*Primary Examiner* — Jason E Flick
(74) *Attorney, Agent, or Firm* — Blank Rome LLP

(57) ABSTRACT

A syringe assembly includes a syringe and a tamper evident cap disposed over a Luer connection of the syringe, the tamper evident cap having a main body that defines a proximal end defining an opening, a distal end opposite the proximal end, an outer surface, and an inner surface opposite the outer surface that defines a passage to receive a tip cap and the Luer connection, where the tamper evident cap is spaced from the tip cap. The main body defines a frangible connection between the proximal and distal ends thereof. The frangible connection can break under a force applied to the distal end of the tamper evident cap such that the proximal end of the tamper evident cap remains engaged with the syringe when the frangible connection breaks. An RFID tag is disposed on the syringe and has an integrated circuit and an antenna configured to send/receive signals between an RFID reader.

21 Claims, 22 Drawing Sheets

Related U.S. Application Data which is a continuation of application No. 16/409,203, filed on May 10, 2019, now Pat. No. 10,661,030.

(60) Provisional application No. 62/772,461, filed on Nov. 28, 2018.

(51) Int. Cl.
*A61M 5/31* (2006.01)
*B65B 3/00* (2006.01)
*A61M 5/32* (2006.01)

(52) U.S. Cl.
CPC ..... *B65B 3/003* (2013.01); *A61M 2005/3104* (2013.01); *A61M 2005/312* (2013.01); *A61M 5/3202* (2013.01); *A61M 2205/584* (2013.01)

(58) Field of Classification Search
CPC .............. A61M 2005/312; A61M 5/50; A61M 2005/3103; A61M 2005/3106; A61M 2005/3114; A61M 2005/3117; A61M 2005/3118; A61M 2207/00; B65B 3/003; B65B 3/04
See application file for complete search history.

(56) References Cited

U.S. PATENT DOCUMENTS

| | | |
|---|---|---|
| 4,667,837 A | 5/1987 | Vitello et al. |
| 5,135,496 A | 8/1992 | Vetter et al. |
| 5,322,515 A | 6/1994 | Karas et al. |
| 5,328,474 A | 7/1994 | Raines |
| 5,554,134 A | 9/1996 | Bonnichsen |
| 5,624,402 A | 4/1997 | Imbert |
| 5,649,622 A | 7/1997 | Hollister |
| 5,680,945 A | 10/1997 | Sander et al. |
| 5,785,691 A | 7/1998 | Vetter et al. |
| 5,833,653 A | 11/1998 | Vetter et al. |
| 5,851,200 A * | 12/1998 | Higashikawa ............ B44F 1/14 604/199 |
| 5,944,699 A | 8/1999 | Barrelle et al. |
| 5,989,227 A | 11/1999 | Vetter et al. |
| 6,193,688 B1 | 2/2001 | Balestracci et al. |
| 6,196,998 B1 | 3/2001 | Jansen et al. |
| 6,330,959 B1 | 12/2001 | Dark |
| 6,432,088 B1 | 8/2002 | Huang et al. |
| 6,485,460 B2 | 11/2002 | Eakins et al. |
| 6,491,665 B1 | 12/2002 | Vetter et al. |
| 6,520,935 B1 | 2/2003 | Jansen et al. |
| 6,585,691 B1 | 7/2003 | Vitello |
| 6,726,652 B2 | 4/2004 | Eakins et al. |
| 6,846,303 B2 | 1/2005 | Eakins et al. |
| 6,942,643 B2 | 9/2005 | Eakins et al. |
| 7,144,238 B2 | 12/2006 | Chao |
| 7,374,555 B2 | 5/2008 | Heinz et al. |
| 7,488,307 B2 | 2/2009 | Rimlinger et al. |
| 7,632,244 B2 | 12/2009 | Buehler et al. |
| 7,806,861 B2 | 10/2010 | Witowski |
| 8,075,535 B2 | 12/2011 | Carrel et al. |
| 8,348,895 B1 | 1/2013 | Vitello |
| 8,353,869 B2 | 1/2013 | Ranalletta et al. |
| 8,591,462 B1 | 11/2013 | Vitello |
| 8,784,377 B2 | 7/2014 | Ranalletta et al. |
| 9,174,010 B2 | 11/2015 | Vedrine |
| 9,480,801 B2 | 11/2016 | Schiller et al. |
| 9,579,463 B2 | 2/2017 | Okihara |
| 9,731,082 B2 | 8/2017 | Vernizeau et al. |
| 9,758,281 B2 | 9/2017 | Glaser et al. |
| 9,821,152 B1 | 11/2017 | Vitello et al. |
| 9,925,340 B2 | 3/2018 | Glocker |
| 9,937,301 B2 | 4/2018 | Ward |
| 10,039,887 B2 | 8/2018 | Sundquist et al. |
| 10,124,122 B2 | 11/2018 | Zenker |
| 10,661,030 B1 | 5/2020 | Murray et al. |
| 11,305,072 B2 | 4/2022 | Murray et al. |
| 11,964,142 B2 | 4/2024 | Murray et al. |
| 2001/0003150 A1 | 6/2001 | Imbert |
| 2003/0014018 A1 | 1/2003 | Giambattista et al. |
| 2004/0116858 A1 | 6/2004 | Heinz et al. |
| 2004/0133169 A1 | 7/2004 | Heinz et al. |
| 2004/0225258 A1 | 11/2004 | Balestracci |
| 2008/0300550 A1 | 12/2008 | Schiller et al. |
| 2009/0283493 A1 | 11/2009 | Witowski |
| 2011/0015578 A1 | 1/2011 | Lowke |
| 2012/0029438 A1 | 2/2012 | Vernizeau et al. |
| 2012/0037266 A1 | 2/2012 | Bochenko |
| 2012/0111368 A1 | 5/2012 | Rahimy et al. |
| 2013/0338604 A1 | 12/2013 | Roedle |
| 2014/0155827 A1 | 6/2014 | Ostrander et al. |
| 2014/0262883 A1 | 9/2014 | Devouassoux et al. |
| 2015/0246185 A1 | 9/2015 | Heinz |
| 2015/0343155 A1 | 12/2015 | Zenker et al. |
| 2016/0001015 A1 | 1/2016 | Kucuk et al. |
| 2016/0151584 A1 | 6/2016 | Deleuil et al. |
| 2016/0184529 A1 | 6/2016 | Okihara |
| 2016/0200484 A1 | 7/2016 | Cosman |
| 2017/0049954 A1 | 2/2017 | Edwards et al. |
| 2018/0273261 A1 | 9/2018 | Qiu |
| 2019/0099557 A1 | 4/2019 | Potdar et al. |
| 2019/0161229 A1 | 5/2019 | Mase |
| 2021/0236736 A1 | 8/2021 | Murray et al. |

FOREIGN PATENT DOCUMENTS

| | | |
|---|---|---|
| EP | 1410819 A1 | 4/2004 |
| EP | 2826508 A1 | 1/2015 |
| EP | 2900301 A1 | 8/2015 |
| EP | 3381492 A1 | 10/2018 |
| JP | 2002315827 A | 10/2002 |
| WO | 2014049097 A1 | 4/2014 |
| WO | 2018024624 A1 | 2/2018 |
| WO | 2020112797 A1 | 6/2020 |
| WO | 2020112807 A1 | 6/2020 |

OTHER PUBLICATIONS

Schreiner press release, Cap-Lock Security Label with RFID Technology | Schreiner Group), "Digital Medication Management plus First-Opening Indication: Cap-Lock Security Label with RFID Technology", https://www.schreiner-group.com/en/company/press/press-releases-label-with-rfid-technology/, Oct. 27, 2020.

* cited by examiner

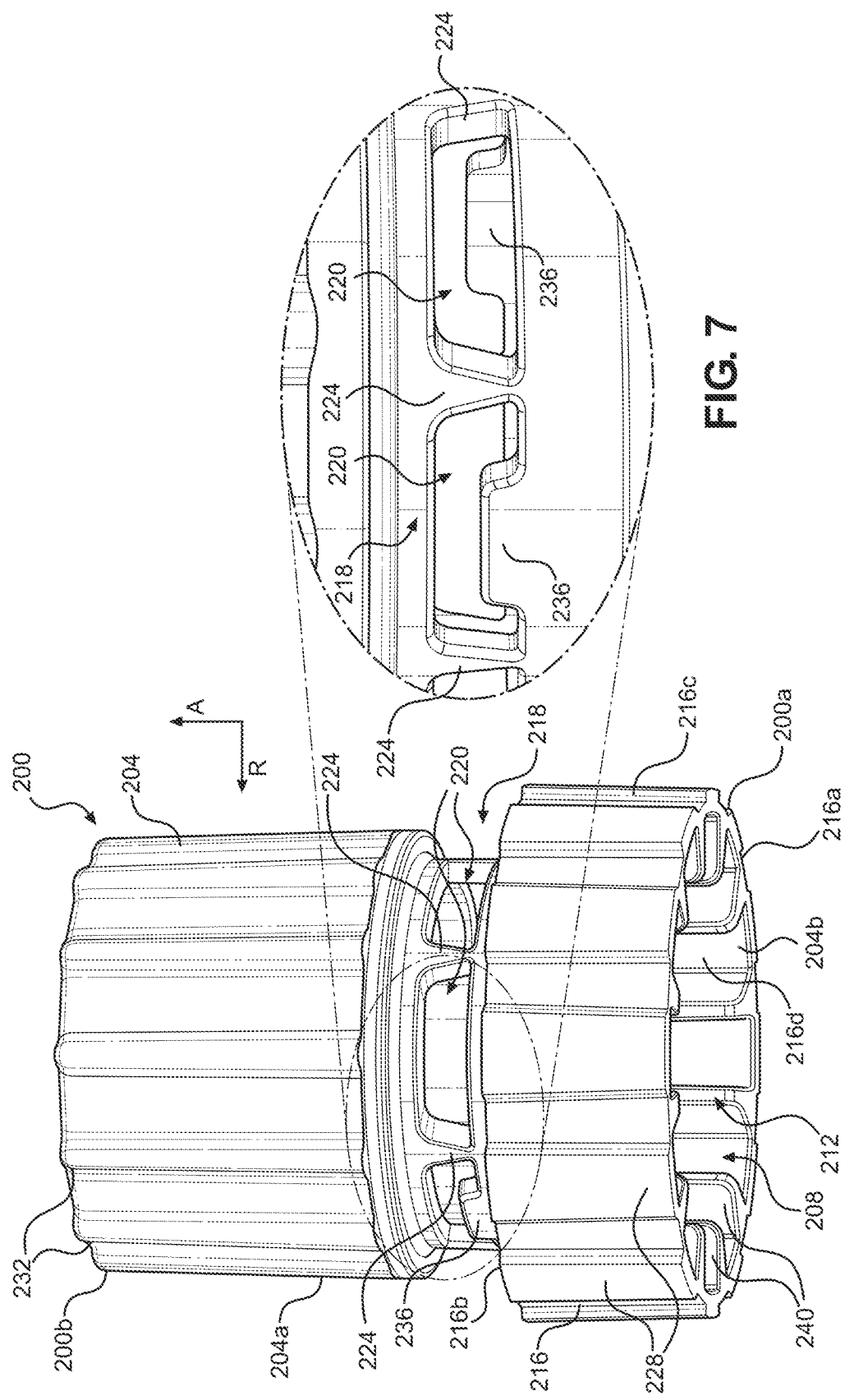

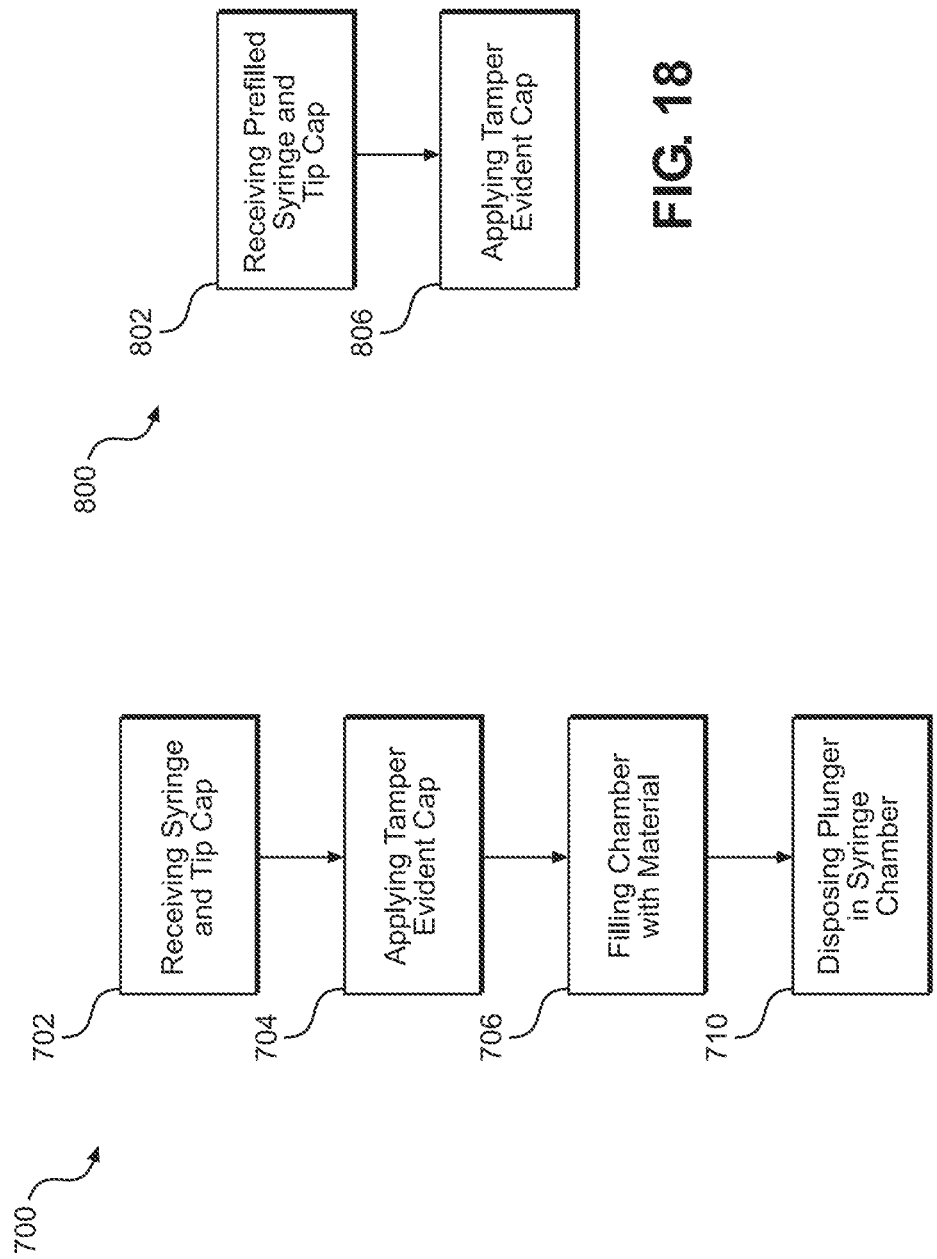

TAMPER EVIDENT CAP WITH RFID FOR SYRINGES

CROSS REFERENCE TO RELATED APPLICATIONS

This application is a continuation-in-part of U.S. patent application Ser. No. 16/850,396, filed Apr. 16, 2020, which is a continuation of U.S. patent application Ser. No. 16/409,203, filed May 10, 2019, which claims the benefit of U.S. Provisional Patent App. No. 62/772,461, filed Nov. 28, 2018, the disclosures of which are hereby incorporated by reference herein.

TECHNICAL FIELD

The present disclosure generally relates to tamper detection devices, and, more particularly, to a tamper evident cap with RFID capabilities for syringes filled with a material.

BACKGROUND

Syringe assemblies are used to hold, transport, and deliver materials. For example, syringes are often utilized in medical environments to administer one or more medicinal materials. Syringe assemblies may differ in size, and their specific dimensions are dictated by the desired application and the specific material to be administered. In some instances, syringes may be pre-filled with one or more materials that are then dispensed from the syringe and combined with other elements.

Many industrial applications require mechanisms that prevent tampering with a particular product. This is especially the case with syringes used in the medical profession, where it is important for medical staff and patients to be aware of any tampering with the syringe or the material contained therein. Existing technology for detecting and preventing tampering is often cumbersome, difficult to use, increases risks of injury to the user, and increase the likelihood of contaminating the patient or the medical environment. Further, the addition of a tampering device can often require changes to be made to the manufacturing process of a syringe or its constituent components, which increases associated production costs and complexity of manufacturing.

Therefore, there is a need for a tamper evident cap configured to be used with syringes having preexisting designs that are filled with a material.

Some industrial applications require identification or tracking of devices and materials. Within the medical field, it is important for staff to be aware of usage parameters of various medical devices or materials for proper storage, handling, and administration to patients. Existing technology for tracking medical devices and materials often relies on manual control and monitoring, which increase the likelihood of human error during the process. The existing technology is not automated, and tracking parameters cannot be easily controlled over the lifetime of the device or material. Furthermore, implementing such control processes after the device or material has been manufactured and prepared requires additional steps to be performed by the medical staff, as well as implementation of separate equipment and operating protocols.

Accordingly, there is a need for an identification and monitoring system configured to be used with medical devices, such as syringes filled with a medical material.

SUMMARY

An embodiment of the present disclosure is a syringe assembly comprising a syringe having a barrel body that extends from a proximal end to a distal end and defines a chamber extending along an axial direction therethrough, and a Luer connection extending from the distal end along the axial direction and defining an outlet in fluid communication with the chamber, where the chamber contains a material. The syringe assembly includes a plunger received within the chamber of the syringe to create a fluid seal within the barrel body and a tip cap defining a central passage configured to receive a portion of the Luer connection such that the tip cap creates a fluid seal over the outlet. The syringe assembly also includes a tamper evident cap disposed over the Luer connection, the tamper evident cap having a main body that defines a proximal end defining an opening, a distal end opposite the proximal end along the axial direction, an outer surface, and an inner surface opposite the outer surface that defines a passage configured to receive the tip cap and the Luer connection, where he tamper evident cap is spaced from the tip cap. The main body further defines a frangible connection between the proximal and distal ends of the main body. The frangible connection is configured to break under a force applied to the distal end of the tamper evident cap such that the proximal end of the tamper evident cap is configured to remain engaged with the syringe when the frangible connection breaks. The syringe assembly further includes a radio-frequency identification (RFID) tag disposed on the syringe and configured to receive and store data related to the syringe assembly, The RFID tag includes an integrated circuit, configured to store electronic information thereon, and an antenna operatively connected to the integrated circuit and configured to receive a signal from an RFID reader to cause transmission of the electronic data to or from the integrated circuit.

Another embodiment of the present disclosure is a method of labeling a syringe assembly. The method comprises providing a label configured to be affixed to a syringe. The label includes a radio-frequency identification (RFID) tag, and the RFID tag has an integrated circuit and an antenna operatively connected to the integrated circuit. The method also includes transmitting a first set of data to the RFID tag and storing the first set of data in a memory of the integrated circuit of the RFID tag. The method further includes verifying the first set of data on the RFID tag. The method also includes transmitting a second set of data to the RFID tag and storing the second set of data in the integrated circuit, the second set of data being different from the first set of data.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In the drawings:

FIG. 6 illustrates a side view of a tamper evident cap of the syringe assembly shown in FIG. 1;

FIG. 7 illustrates an expanded view of the encircled portion of the tamper evident cap shown in FIG. 6;

FIG. 17 illustrates a process flow diagram of a method of filling a syringe with material according to another embodiment of the present disclosure;

FIG. 18 illustrates a process flow diagram of a method of applying a tamper evident cap to a prefilled syringe according to an embodiment of the present disclosure;

DETAILED DESCRIPTION OF ILLUSTRATIVE EMBODIMENTS

Figure 1:
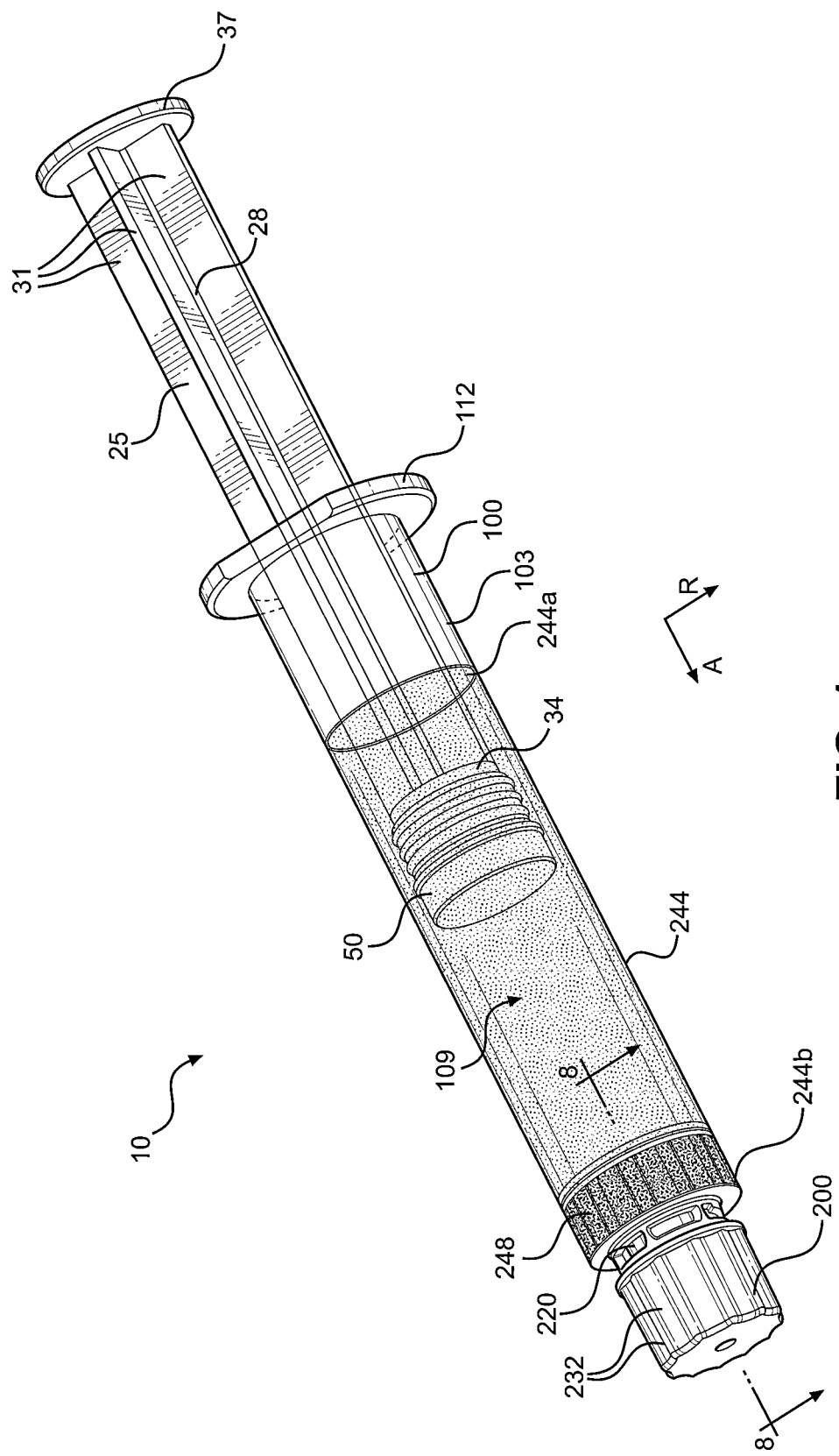
FIG. 1 illustrates a perspective view of a syringe assembly in accordance with an embodiment of the present disclosure.
Figure 2:
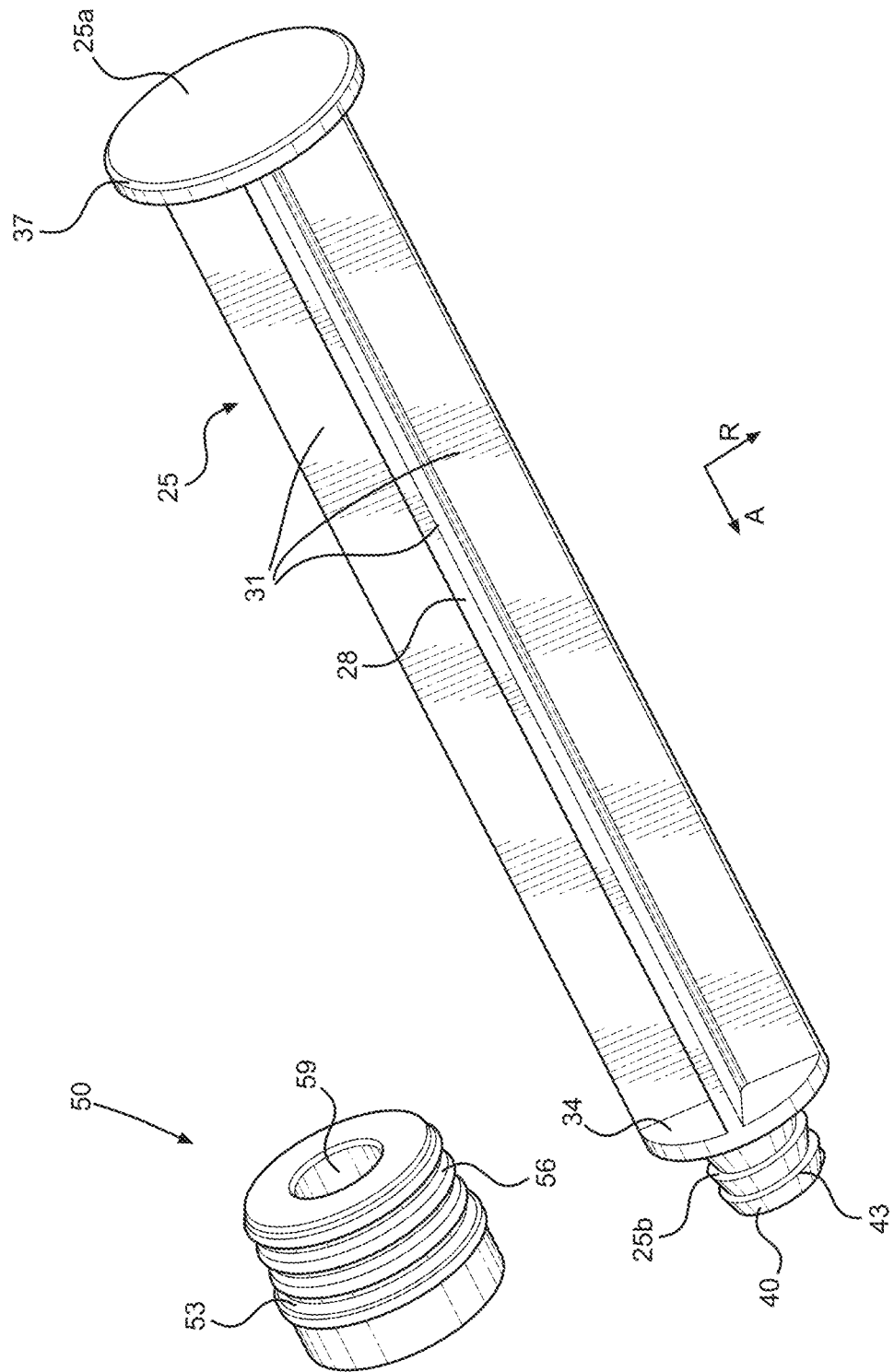
FIG. 2 illustrates a perspective view of a plunger rod and plunger of the syringe assembly shown in FIG. 1.
Figure 3:
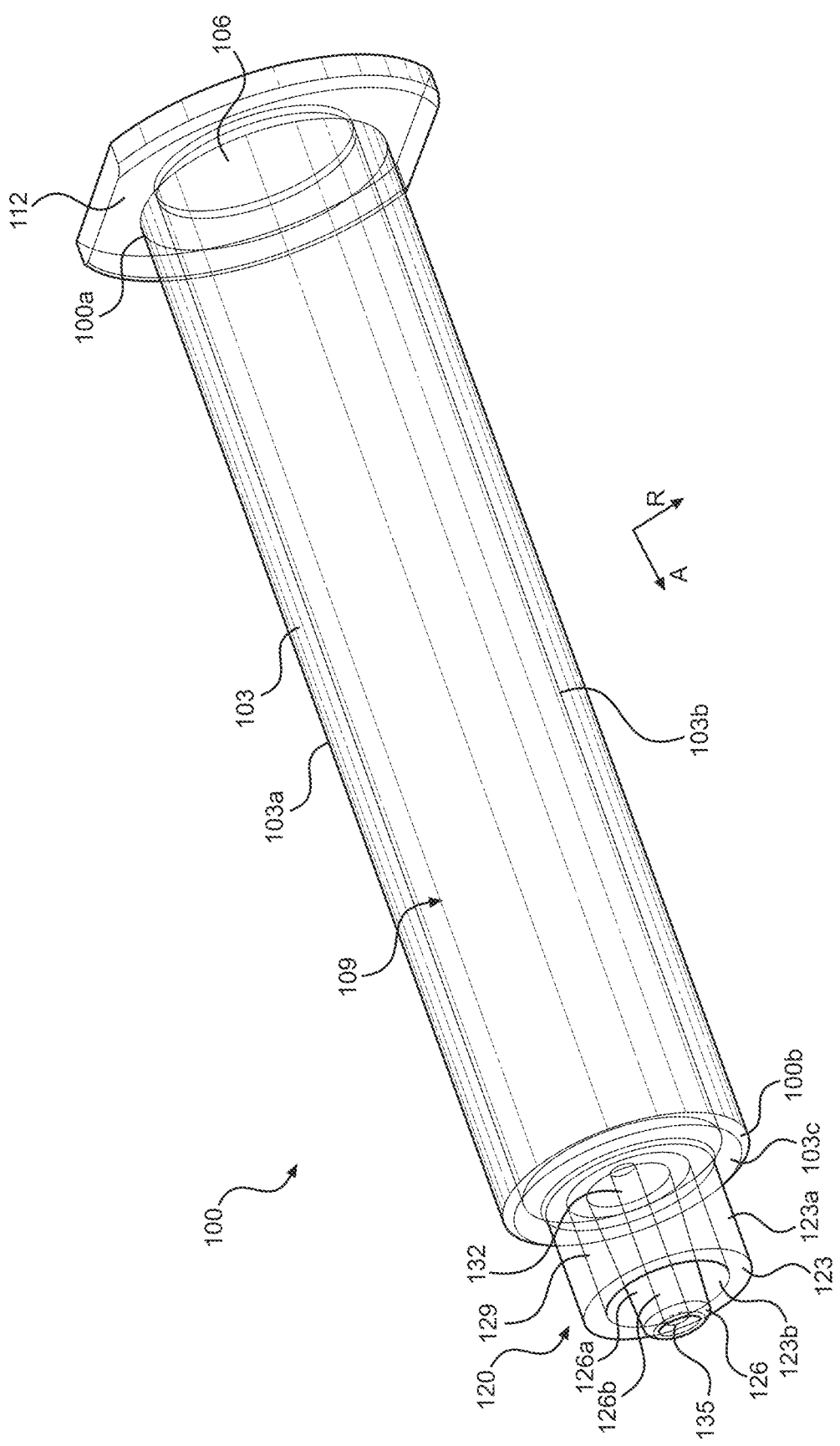
FIG. 3 illustrates a perspective view of a syringe of the syringe assembly shown in FIG. 1.
Figure 4A:
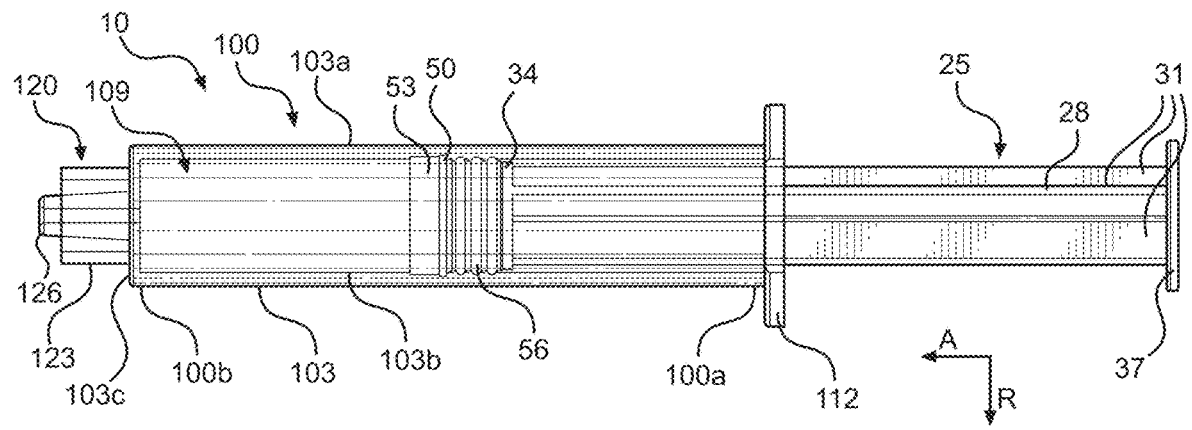
FIG. 4A illustrates a side view of the syringe assembly shown in FIG. 1 with certain components removed for clarity, with the plunger and plunger rod in a first position.
Figure 4B:
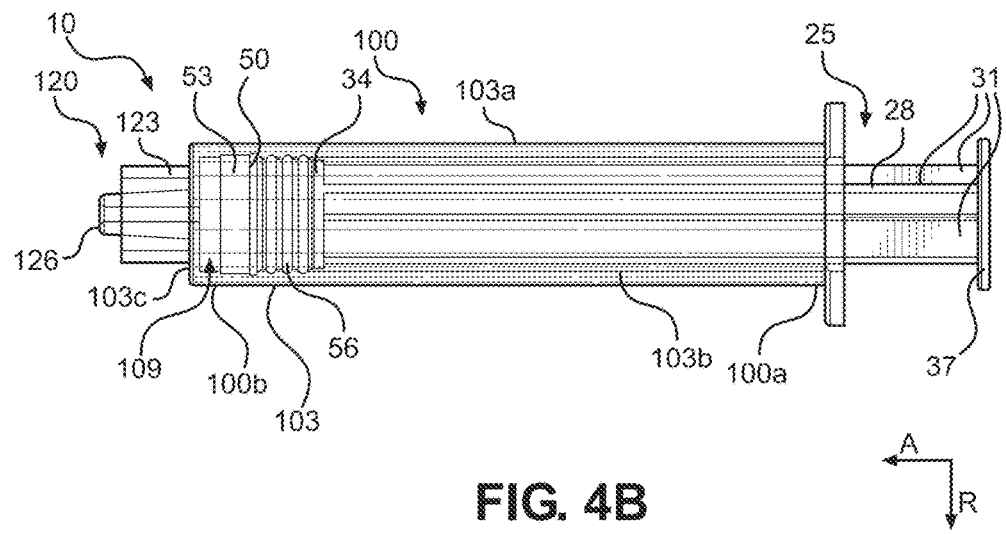
FIG. 4B illustrates a side view of the syringe assembly shown in FIG. 1 with certain components removed for clarity, with the plunger and plunger rod in a second position.

Described herein is a syringe assembly 10, 10' that includes a tamper evident cap 200. Certain terminology is used to describe the syringe assembly 10, 10' in the following description for convenience only and is not limiting. The words "right," "left," "lower," "upper," "proximal," and "distal" designate directions in the drawings to which reference is made. The words "inner" and "outer" refer to directions toward and away from, respectively, the geometric center of the description to describe the syringe assembly 10, 10' and related parts thereof. The words "axially" and "radially" refer to directions along the orthogonal axial and radial directions A, R, respectively. The terminology includes the above-listed words, derivatives thereof and words of similar import.

Referring to FIGS. 1-4B, the syringe assembly 10 includes a syringe 100 having a barrel body 103. The barrel body 103 can extend from a proximal end 100a to a distal end 100b along the axial direction A, and can be molded from a plastic. In one embodiment, the barrel body 103 can comprise a substantially transparent material, such that a user of the syringe assembly 10 can monitor the material levels within the barrel body 103, though barrel bodies 103 having various levels of opacity are contemplated. The barrel body 103 is depicted as comprising a substantially cylindrical shape, though the present disclosure is not intended to be limited to such. The barrel body 103 can be comprised of cyclic olefin copolymer (COC), cyclic olefin polymer (COP), glass, or various other materials. The barrel body 103 can have an outer surface 103a that extends from the proximal end 100a to the distal end 100b along the axial direction A, an inner surface 103b opposite the outer surface 103a that also extends from the proximal end 100a to the distal end 100b along the axial direction A, and a distal surface 103c that extends along the radial direction R at the distal end 100b of the barrel body 103. The inner surface 103b of the barrel body 103 defines a chamber 109 that extends along the axial direction A from an opening 106 at the proximal end 100a to the Luer connection 120 at the distal end 100b, where the Luer connection 120 will be discussed further below. The chamber 109 is configured to receive and store a material, such as a liquid, for dispensing through the tip 126. The syringe 100 also includes a flange 112 extending radially outwards from the proximal end 100a of the barrel body 103, where the function of the flange 112 will be described further below. Though depicted as defining an oval shape with two flat, oppositely positioned sides, the flange 112 can define other shapes as desired.

The chamber 109 can be sized and configured to receive a plunger 50, such that the plunger 50 is capable of sliding along the axial direction A through the chamber 109. The plunger is configured to define the proximal-most extent to which the material can travel through the chamber 109. The plunger 50 can have a substantially cylindrical body 53, though the shape of the body 53 will generally conform to the shape of the chamber 109. The body 53 can be comprised of a substantially flexible material such as rubber, though other embodiments are contemplated where the plunger defines other materials. The plunger 50 can further include a plurality of ridges 56 extending radially outwards from the body 53. As shown, the plurality of ridges 56 extend substantially circumferentially around the body 53 and are aligned and spaced apart along the axial direction A. However, the ridges 56 can comprise different sizes, shapes, and arrangements in other embodiments. The ridges 56 can function to engage the inner surface 103b of the barrel body 103 of the syringe 100 so as to create a fluid seal between the plunger 50 and the syringe 100. As the plunger 50 moves distally through the chamber 109 (such as from a first position shown in FIG. 4A to a second position shown in FIG. 4B), the plunger 50 can function to push material out of the chamber 109 through the tip 126. Alternatively, as the plunger 50 moves proximally through the chamber 109, the plunger 50 can function to draw material into the chamber 109 through the tip 126.

The plunger 50 can define a bore 59 that extends into the body 53 from its proximal end. The bore 59 can be configured to engage a portion of a plunger rod 25, which allows a user of the syringe assembly 10 to manually move the plunger 50 through the chamber 109 of the syringe 100 along the axial direction A. The plunger rod 25 extends from a proximal end 25a to a distal end 25b opposite the proximal end 25a along the axial direction A. The plunger rod 25 can comprise a rod body 28 at its center, where the rod body 28 comprises an elongated, axially-extending rod. Connected to the rod body 28, the plunger rod 25 can include a plurality of walls 31 extending radially outwards from the rod body 28. As depicted, each of the walls 31 defines a substantially rectangular body that extends radially outwards from the rod body 28 and axially along the length of the rod body 28. The plunger rod 25 is shown as including four walls 31, where the walls 31 are arranged about the rod body 28 circumferentially spaced apart 90 degrees, such that the arrangement of walls 31 forms a substantially plus-shaped orientation. However, the plunger rod 25 can include more or less walls 31 in other embodiments, and thus other arrangements of walls 31 can define other shapes. Additionally, it is contemplated that the walls 31 can define other shapes or extend to different extents along the axial length of the rod body 28 or radially outwards from the rod body 28. The walls 31 define a height along the radial direction R that is less than the diameter of the chamber 109, so that the plunger rod 25 can freely move along the axial direction A within the chamber 109, and the walls 31 may or may not contact the inner surface 103b of the syringe 100. The walls 31 can function to provide stability and strength to the plunger rod 25, while minimizing the cross-sectional footprint of the plunger rod 25 so as to reduce material requirements for the plunger rod 25, thus reducing overall weight of the syringe assembly 10.

The rod body 28, as well as the walls 31, can extend from a first flange 34 positioned at the distal end 25b of the plunger rod 25 to a second flange 37 positioned at the proximal end 25a of the plunger rod 25. Each of the first and second flanges 34, 37 can be substantially cylindrically shaped, though other shapes are contemplated. The plunger rod 25 can also include a connection extension 40 that extends from the distal end 25b along the axial direction A from the first flange 34 in a direction opposite the rod body 28. The connection extension 40 is configured to be received within the bore 59 of the plunger 50 so as to couple the plunger 50 to the distal end 25b of the plunger rod 25. To strengthen this connection, the connection extension 40 can define a plurality of barbs 43 extending outwards along the radial direction R. The barbs 43 increase in diameter as they extend proximally along the axial length of the connection extension 40. These barbs 43 allow the connection extension 40 to be easily inserted into the bore 59 of the plunger 50 in a first axial direction, but upon attempted removal of the connection extension 40 from the bore 59, the barbs 43 will engage the wall of the bore 59, thus preventing disengagement of the plunger 50 from the plunger rod 25. Though one method of engagement between the plunger 50 and plunger rod 25 is shown, other methods are contemplated, such as forming the plunger 50 onto the plunger rod 25, a simple interference fit, threaded engagement, snap-fit, etc.

Once the plunger 50 and the distal end 25b of the plunger rod 25 are inserted into the chamber 109 of the syringe 100, the proximal end 25a of the plunger rod 25 being located outside the chamber 109, the plunger rod 25 can be used to control dispensing of the material from within the chamber 109. In operation, movement of the plunger rod 25, and thus the plunger 50, distally through the chamber 109 along the axial direction A forces material to flow out of the chamber 109 through the tip 126. To do this, a user can, using one hand, pull the flange 112 of the syringe 100 and the second flange 37 of the plunger rod 25 towards each other. Conversely, movement of the plunger rod 25, and thus the plunger 50, proximally through the chamber 109 along the axial direction A draws material into the chamber 109 through the tip 126. To do this, a user can, using one or two hands, push the flange 112 of the syringe 100 and the second flange 37 of the plunger rod 25 away from each other.

Referring to FIGS. 3-5 and 8, the Luer connection 120 of the syringe 100 will be described in greater detail. The Luer connection 120 can extend from the distal end 100b of the barrel body 103 along the axial direction A. In particular, the Luer connection 120 can extend from the distal surface 103c of the barrel body 103 along the axial direction A. At the center of the Luer connection 120, the Luer connection 120 includes a tip 126 that extends from the distal end 100b of the barrel body 103 along the axial direction A. As depicted, the tip 126 takes the form of a tapered, hollow tube, though other embodiments of the tip 126 are contemplated, such as a cylindrical, hollow tube. The tip 126 has an outer surface 126a and an inner surface 126b opposite the outer surface 126a, where the inner surface 126b defines a passage 132 that extends through the tip 126. The passage 132 can extend from the chamber 109 of the syringe 100 to an outlet 135 of the Luer connection 120. As the passage 132 and the outlet 135 are in fluid communication with the chamber 109, the passage 132 and the outlet 135 thus define the pathway for material being dispensed from the chamber 109 of the syringe 100.

The Luer connection 120 further includes an outer wall 123 that extends from the distal end 100b of the barrel body 103 along the axial direction A. As depicted, the outer wall 123 takes the form of a substantially cylindrical, hollow tube, though other embodiments of the outer wall 123 are contemplated, such as a tapered, hollow tube. The outer wall 123 has an outer surface 123a and an inner surface 123b opposite the outer surface 123a. As depicted, the outer surface 123a is smooth, though other embodiments of the outer surface 123a are contemplated, e.g., ridged or otherwise textured. Similarly, the inner surface 123b is depicted as smooth, though other embodiments of the inner surface 123b also are contemplated, e.g., threaded (female or male). The outer wall 123 extends circumferentially around the tip 126, such that the inner surface 123b of the outer wall 123 faces the outer surface 126a of the tip 126. As a result, a gap 129 can be defined between the outer wall 123 and the tip 126, specifically between the inner surface 123b of the outer wall 123 and the outer surface 126a of the tip 126. The gap 129 can be configured to receive a portion of the tip cap 150, as will be described further below.

Figure 5:
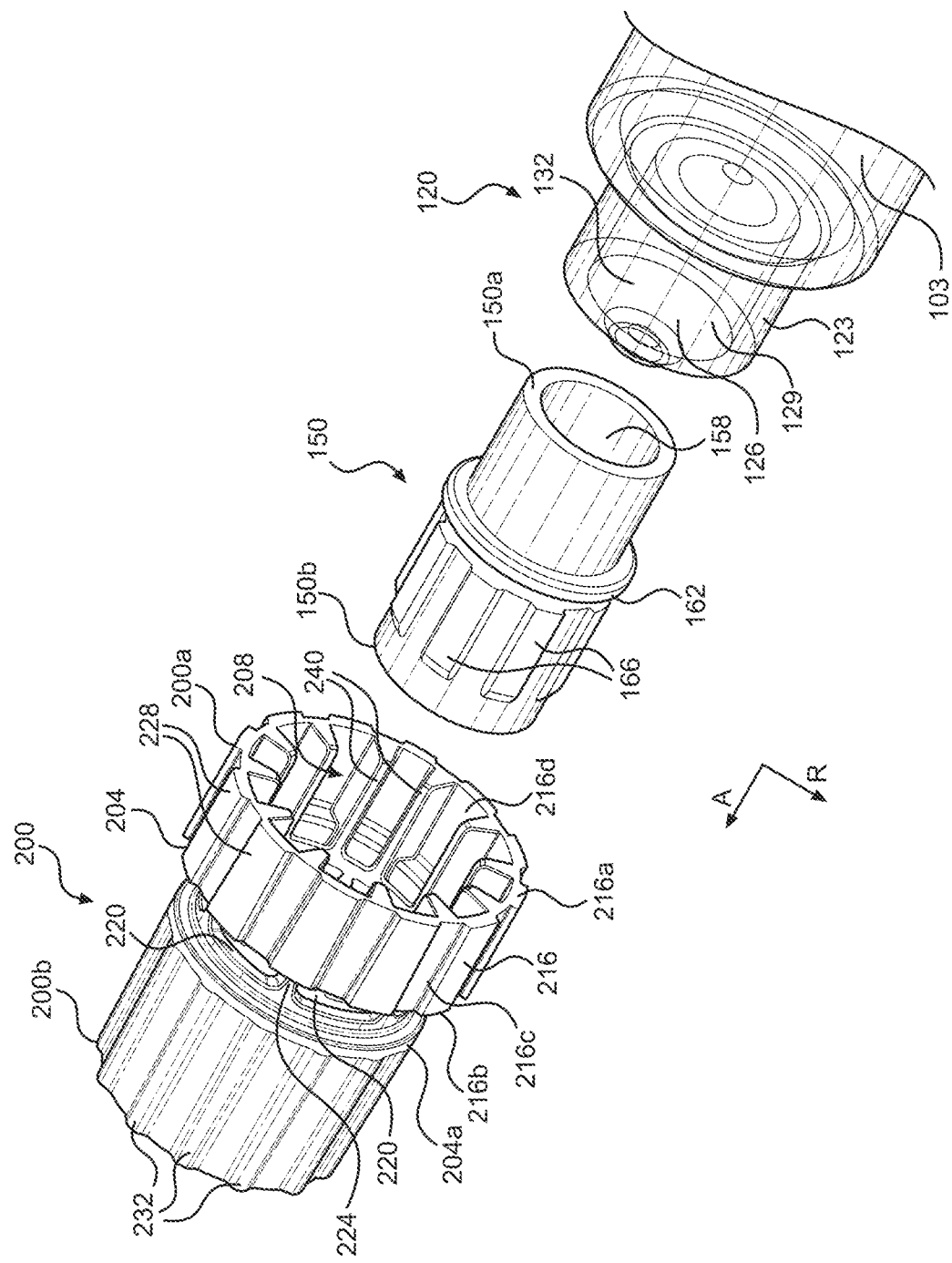
FIG. 5 illustrates an exploded view of a distal portion of the syringe assembly shown in FIG. 1.
Figure 8:
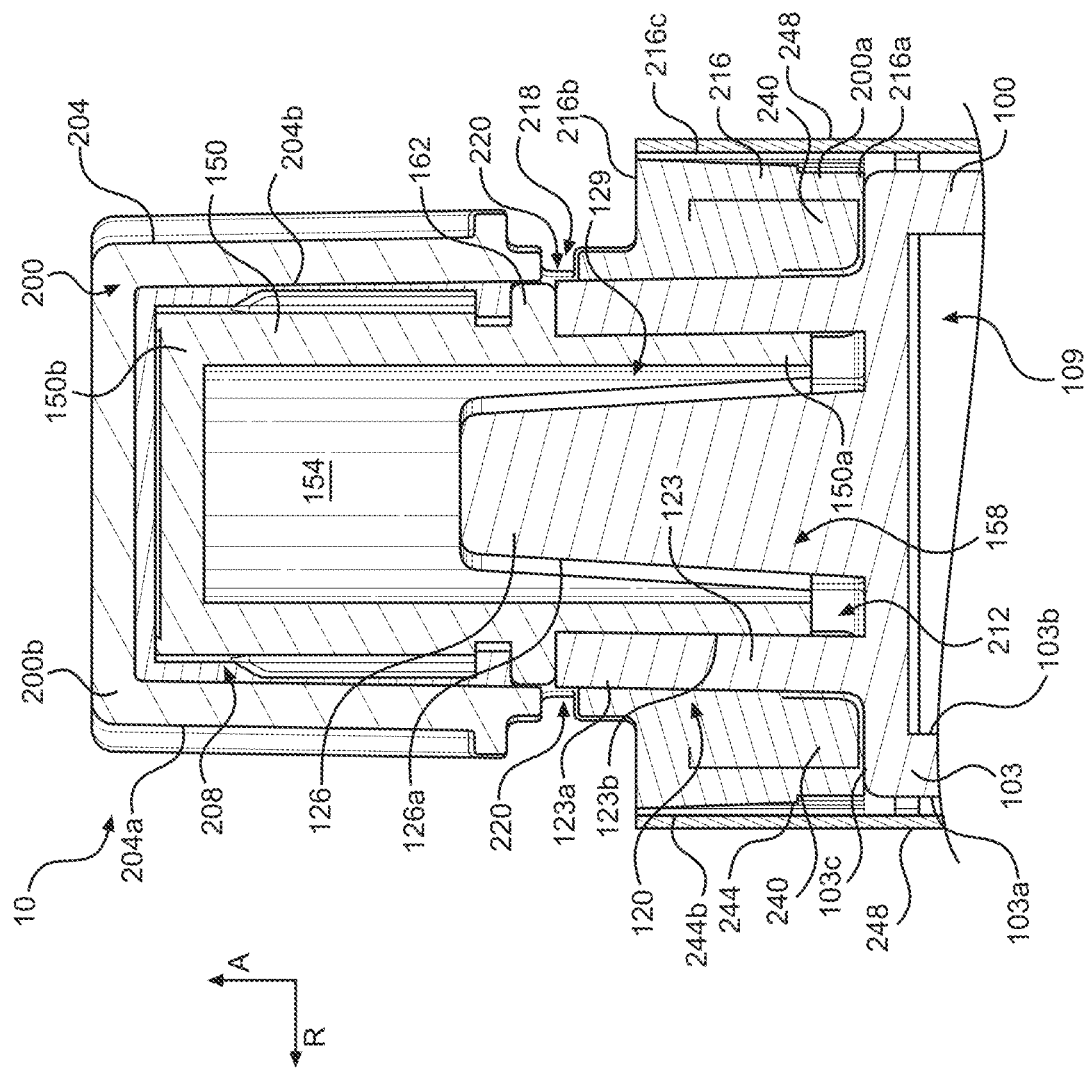
FIG. 8 illustrates a cross-sectional view of a distal portion of the syringe assembly shown in FIG. 1, taken along line 8-8 shown in FIG. 1.

Now referring to FIGS. 5 and 8, after the syringe 100 has been filled, the outlet 135 needs to be sealed so as to prevent material from leaking out of the chamber 109. To do this, a tip cap 150 can be attached to the Luer connection 120 so as to seal the outlet 135. The tip cap 150 can extend from a proximal end 150a to a distal end 150b opposite the proximal end 150a along the axial direction A. As depicted, the proximal end 150a defines an opening 158, whereas the distal end 150b is closed. The tip cap 150 can define a central passage 154 extending along the axial direction A into the tip cap 150 from the opening 158. The tip cap 150 can further define a ridge 162 extending radially outwards from the outer surface of the tip cap 150, and substantially continuously around the entirety of the perimeter of the tip cap 150. However, in other embodiments, the ridge 162 may only extend partially around the perimeter of the tip cap 150, or may not be present at all. Further, a plurality of ribs 166 can extend radially outwards from the outer surface of the tip cap 150 distal to the ridge 162. The ribs 166 can be arranged circumferentially around the tip cap 150 so as to provide a texture for grasping by a user of the syringe assembly 10. Though one embodiment of ribs 166 are shown, the present disclosure is not intended to be limited to such.

In operation, as stated previously, the tip cap 150 is configured to be attached to the Luer connection 120 of the syringe 100 so as to create a fluid seal over the outlet 135. To accomplish this, after the syringe 100 has been filled during assembly, the tip cap 150 can be pushed into the Luer connection 120 with a force along the axial direction A, such that the central passage 154 of the tip cap 150 receives the tip 126 of the Luer connection 120 and the portion of the tip cap 150 proximal to the ridge 162 is disposed in the gap 129 defined between the outer wall 123 and the tip 126. Due to spacing of the wall 123 and tip 126 and the thickness of the tip cap 150, as well as the diameter of the passage 132 of the tip cap 150 relative to the diameter of the tip 126, the tip cap 150 can be secured to the Luer connection 120 through an interference fit. In other embodiments, the inner surface 123b comprises threads (female or male), the external portion of the tip cap 150 proximal to the ridge 162 comprises complementary threads, and the tip cap 150 is secured to the Luer connection 120 through a screw-in fit. The ridge 162 can contact the upper surface of the outer wall 123 so as to limit the extent to which the tip 126 can be disposed in the passage 132. Once disposed into the Luer connection 120, the outlet 135 can be located at a distal-most part of the passage 132 and the tip 126 can engage the inner surface of the passage 132, thus creating a fluid seal over the outlet 135.

Now referring to FIGS. 1 and 5-8, the tamper evident cap 200 will be discussed in detail. The tamper evident cap 200 can include a main body 204 that extends from a proximal end 200a to a distal end 200b opposite the proximal end 200a along the axial direction A. The main body 204 can be configured as a substantially hollow cylinder, though other shapes are contemplated, as the shape of the tamper evident cap 200 can vary according to the shape of the syringe 100, and specifically the Luer connection 120. The tamper evident cap 200 can be formed through injection molding, and can comprise a plastic such as medical grade polypropylene, polycarbonate, or polyethylene terephthalate. However, other methods of forming the tamper evident cap 200 and other materials for forming the tamper evident cap 200 are contemplated. The main body 204 defines an outer surface 204a and an inner surface 204b opposite the outer surface 204a, where the inner surface 204b defines a passage 208 configured to receive the Luer connection 120 and the tip cap 150. The distal end 200b of the main body 204 can be closed, whereas the proximal end 200a can define an opening 212, where the passage 208 extends from the opening 212 along the axial direction A and terminates within the main body 204 at a location proximal to the distal end 200b.

However, in other embodiments the distal end 200b of the main body 204 can be open. In yet other embodiments, the distal end 200b of the main body 204 can be partially closed.

The proximal end 200a of the main body can define a collar 216 that substantially surrounds the Luer connection 120 when the tamper evident cap 200 is disposed over the Luer connection 120, as will be discussed further below. As depicted, the collar 216 defines a substantially annular disc, though it is contemplated that the collar 216 can define other shapes as desired. The collar 216 can have a proximal surface 216a, a distal surface 216b opposite the proximal surface 216a along the axial direction A, an outer surface 216c that extends from the proximal surface 216a to the distal surface 216b, and an inner surface 216d opposite the outer surface 216c. In the depicted embodiment, the outer surface 216c of the collar 216 can comprise a portion of the outer surface 204a of the main body 204, and the inner surface 216d can comprise a portion of the inner surface 204d of the main body 204. The collar 216 can define a plurality of internal ribs 240 that extend radially inwards from the inner surface 216d and are positioned circumferentially around the inner surface 216d. Though one particular number and arrangement of internal ribs 240 is shown, other numbers and arrangements are contemplated. For example, though the internal ribs 240 are depicted as being substantially equidistantly spaced apart, non-equidistant spacing of the internal ribs 240 is contemplated. In other embodiments, the inner surface 216d is substantially smooth, i.e., lacking any internal ribs.

In operation, the tamper evident cap 200 can be attached to the syringe 100 by pressing the tamper evident cap 200 over the Luer connection 120 and the tip cap 150 via a force applied along the axial direction A. The internal ribs 240 can be configured such that, when this occurs, the internal ribs 240 of the tamper evident cap 200 form an interference fit with the Luer connection 120, specifically the outer surface 123a of the outer wall 123 of the Luer connection 120. This interference fit can cause the tamper evident cap 200, and particularly the proximal end 200a, to resist disengagement from the Luer connection 120 as a result of a distally or rotationally applied force to the tamper evident cap 200. In addition to the interference fit, in other embodiments it is contemplated that the collar 216 can be attached to the Luer connection 120 and/or another portion of the syringe 100 via a sonic weld, adhesive, gripping material, etc. In certain embodiments, the tamper evident cap 200 is further secured to the Luer connection 120 by a film 244 disposed over the collar 216 or a portion thereof, as discussed further below.

In some embodiments, the proximal surface 216a of the collar 216 can abut the distal surface 103c of the syringe 100 when the tamper evident cap 200 is fully disposed over the Luer connection 120. This can function to limit the axial movement of the tamper evident cap 200 in relation to the syringe 100 and indicate to the user of the syringe assembly 10 that the tamper evident cap 200 is fully in place. Notably, the outer diameter of the collar 216 may not extend out past the outer diameter of the outer surface 103a of the barrel body 103, and as well as not extend proximally past the distal surface 103c. As a result, the collar 216 can be spaced in an entirety from the outer surface 103a of the barrel body 103. Because of this, a user of the syringe assembly 10 maintains a complete line of sight to the material within the chamber 109 of the syringe 100, thus allowing the user to be constantly aware of the amount of material within the syringe 100. The collar 216 does not prevent the user from viewing any portion of the material within the chamber 109, as well as the distal end of the plunger 50 to determine whether material is still trapped within the chamber 109 between the plunger 50 and the syringe 100. In other embodiments, the proximal surface 216a of the collar 216 can approach, but not abut, the distal surface 103c of the syringe 100 when the tamper evident cap 200 is fully disposed over the Luer connection 120, thereby forming a gap between the proximal surface 216a of the collar 216 and the distal surface 103c of the syringe 100. In yet other embodiments, the proximal surface 216a of the collar 216 can overlap the distal surface 103c of the syringe 100 when the tamper evident cap 200 is fully disposed over the Luer connection 120.

In certain embodiments, when the tamper evident cap 200 is attached to the Luer connection 120, the tamper evident cap 200 can be spaced in an entirety from the tip cap 150, such that a gap is formed between the tamper evident cap 200 and the tip cap 150 and no portion of the tamper evident cap 200 contacts the tip cap 150. This lack of engagement between the tamper evident cap 200 and the tip cap 150 allows the tamper evident cap 200 to be used simply with existing syringe 100 and tip cap 150 assemblies without interfering with the seal the tip cap 150 creates with the Luer connection 120. Other tamper evident cap designs can require complete redesign of the syringe and/or tip cap, which requires additional tooling for manufacture, thus increasing total manufacturing cost and complexity. The tamper evident cap 200 of the present applications presents none of these difficulties. Additionally, this spacing prevents the distal end 200b of the tamper evident cap 200 from being reattached to the syringe assembly 10 after the frangible connection 218 between the proximal and distal ends 200a, 200b has broken, as will be discussed below.

However, in other embodiments, a portion of the tamper evident cap 200 is in contact with the tip cap 150. For example, in some embodiments, the inner surface 204b at the distal end 200b can contact the distal end 150b of the tip cap 150 when the tamper evident cap 200 is fully disposed over the Luer connection 120. In other embodiments, at least a portion of the inner surface 204b along the axial direction A between the frangible connection 218 and the distal end 200b of the tamper evident cap 200 contacts an outer surface of the tip cap 150 when the tamper evident cap 200 is fully disposed over the Luer connection 120. Preferably, any contact between the tamper evident cap 200 and the tip cap 150 is such that the fluid seal over the outlet 135 is not compromised by the attachment of the tamper evident cap 200 to the syringe 100 or the decoupling of the distal end 200b upon breakage of the frangible connection 218.

Continuing with FIGS. 1 and 5-8, the tamper evident cap 200 can include a frangible connection 218 positioned axially between the proximal and distal ends 200a, 200b of the main body 204. The frangible connection 218 is configured to be the portion of the tamper evident cap 200 that enables the tamper evident cap 200 to indicate to a user whether the syringe assembly 10 has been tampered with. When the tamper evident cap 200 is attached to the Luer connection 120, the frangible connection 218 is configured to break under a force applied to the distal end 200b of the main body 204. This force can be a clockwise or counter-clockwise rotational force, or any other force as desired. As a result, the distal end 200b will be decoupled from the proximal end 200a, and the proximal end 200a of the main body 204 will remain attached to the Luer connection 120 of the syringe 100 as when the frangible connection 218 breaks. The frangible connection 218 is thus designed such that the force required to break the frangible connection 218 is less than the force required to decouple the proximal end 200a from the Luer connection 120. If a user of the syringe assembly 10 sees that the frangible connection 218 of the tamper evident cap 200 is broken, the user knows that the material within the chamber 109 of the syringe 100 may have been tampered with. However, if the frangible connection 218 is intact, the user can be assured of a greatly reduced risk that the material has been tampered with.

The frangible connection 218 comprises a plurality of frangible bridges 224 positioned circumferentially around the main body 204. The frangible bridges 224 can be positioned around an entirety of the circumference of the main body 204, such that when the frangible connection 218 breaks, the distal end 200b of the main body 204 can be completely separated from the proximal end 200a. Each of the frangible bridges 224 can comprise a thin portion of the main body 204 that tapers inwards in width as it extends proximally. However, it is contemplated that the frangible bridges 224 can be alternatively configured. For example, the frangible bridges 224 can be configured as substantially elongate body portions having a constant width. Further, the frangible bridges 224 can be equidistantly spaced about the circumference of the main body 204.

The frangible connection 218 can also define a plurality of gaps 220 that extend through the main body 204 from the outer surface 204a to the inner surface 204b, where a gap 220 can extend circumferentially between two frangible bridges 224. Though each of the gaps 220 is shown as having a particular design, each of the gaps 220 can vary in design and spacing along with the design and spacing of each frangible bridge 224. The inclusion of the frangible bridges 224 and gaps 220 allows the tamper evident cap 200 to be easily broken at the frangible connection 218. The tamper evident cap 200 can also include at least one protrusion 236 that extends distally into the gap 220, where the protrusion 236 can be useful during the injection molding of the tamper evident cap 200. For example, the depicted tamper evident cap 200 includes two protrusions 236, though more or less than two protrusions are contemplated. Also, embodiments of the tamper evident cap 200 without the protrusions 236 are contemplated.

The tamper evident cap 200 can also include a plurality of external ribs 228 that extend outwards from the outer surface 204a of the main body 204 at the proximal end 200a along the radial direction. Each of the external ribs 228 can substantially define a rectangular prism, and the external ribs 228 can be equidistantly spaced circumferentially around the proximal end 200a of the main body 204. However, it is contemplated that the external ribs 228 can define alternate shapes, or can be non-equidistantly spaced around the proximal end 200a of the main body 204. The external ribs 228 can be configured to secure a film 244 to the collar 216 of the tamper evident cap 200, as will be discussed further below. The tamper evident cap 200 can also include a plurality of ribs 232 that extend outwards from the outer surface 204a of the main body 204 at the distal end 200b along the radial direction. As depicted, each of the ribs 232 can define a substantially hemispherical extension, and each of the ribs 232 can be equidistantly spaced circumferentially around the distal end 200b of the main body 204. However, it is contemplated that the ribs 232 can define alternate shapes, or can be non-equidistantly spaced around the distal end 200b of the main body 204. The ribs 232 can allow for the distal end 200b of the main body 204 to be easily grasped by a user so as to allow the user to twist the tamper evident cap 200 to break the frangible connection 218.

Figure 9:
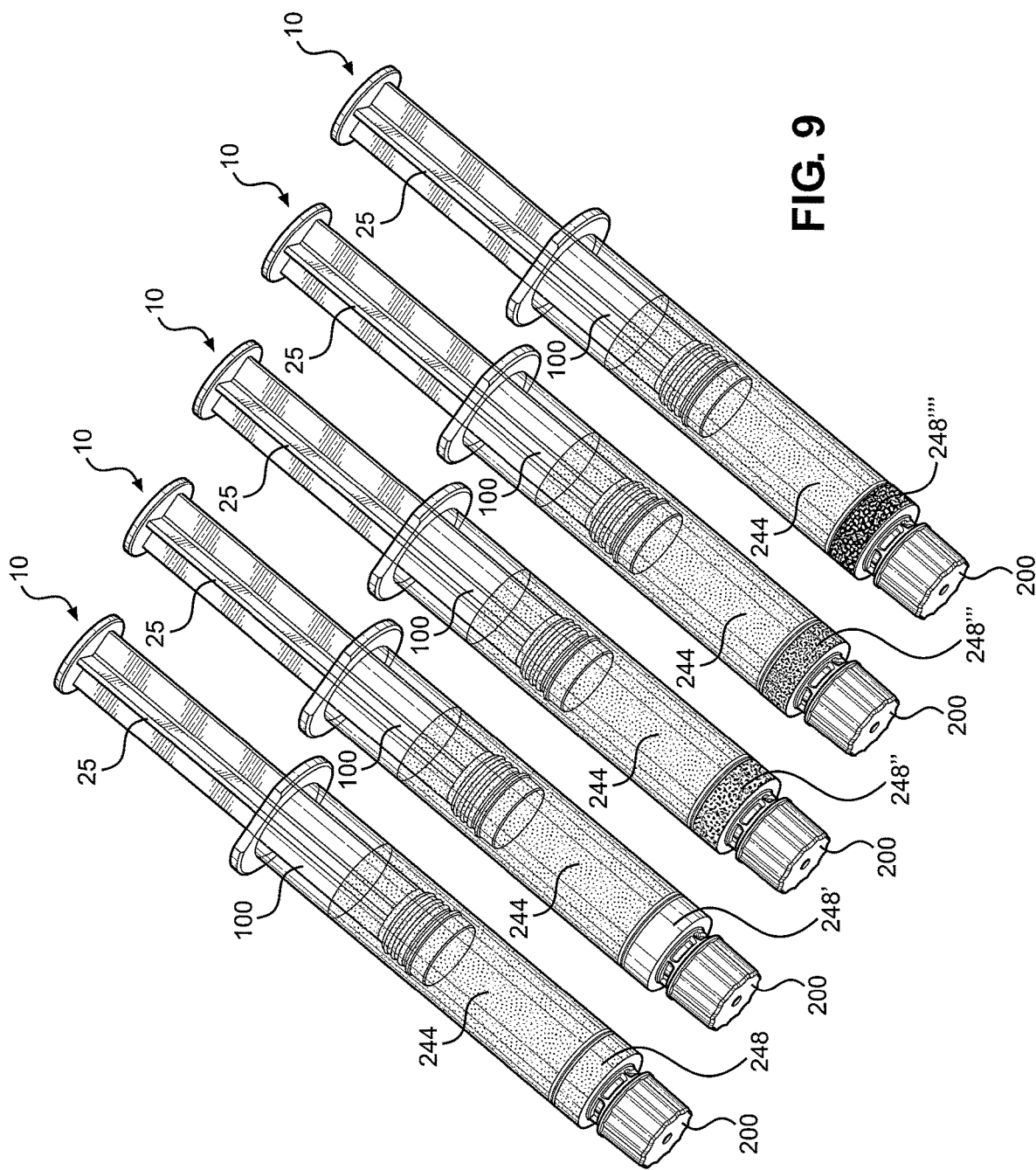
FIG. 9 illustrates a plurality of the syringe assemblies shown in FIG. 1, each including films with different color-coded portions according to an embodiment of the present disclosure.
Figure 10:
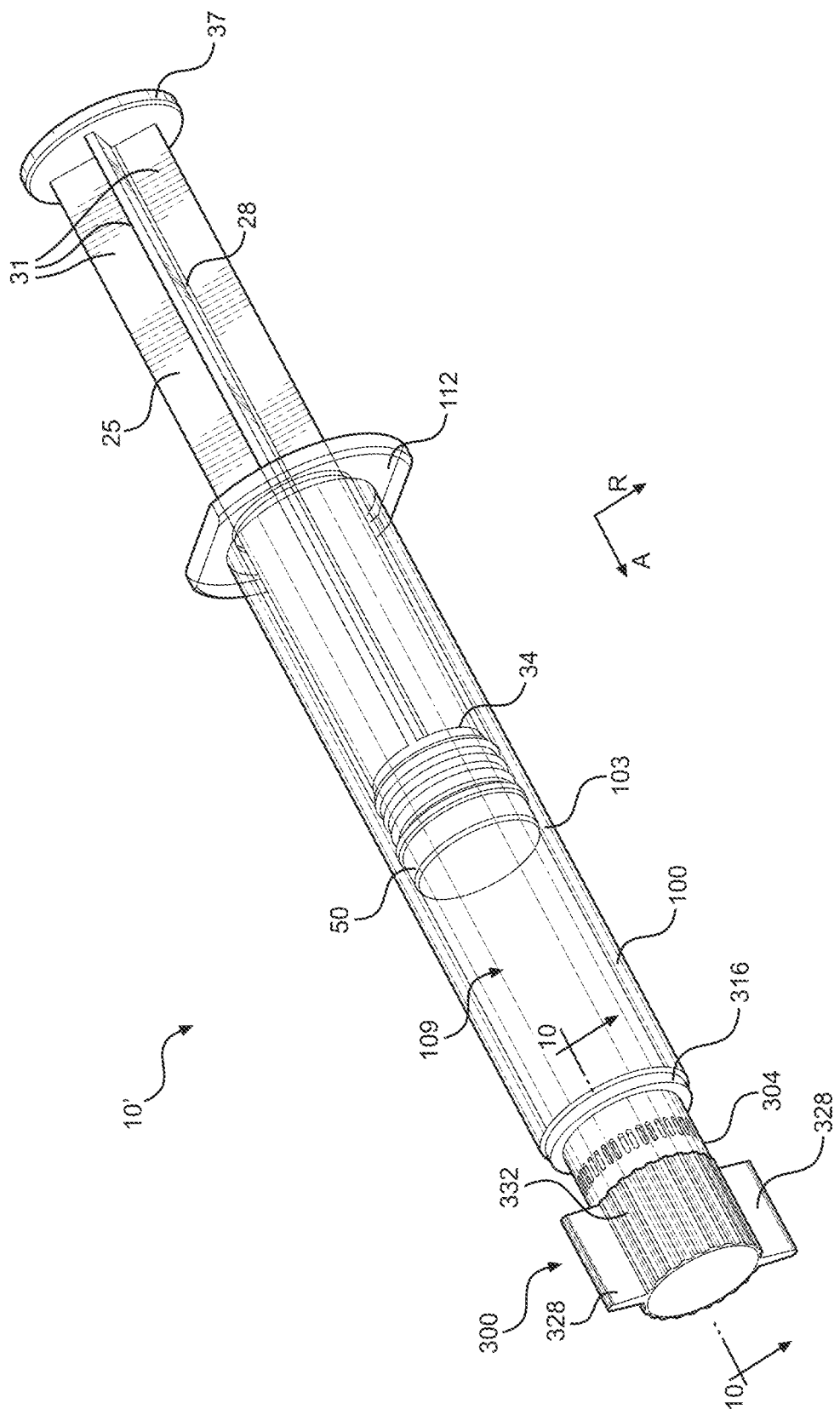
FIG. 10 illustrates a perspective view of a syringe assembly in accordance with another embodiment of the present disclosure.
Figure 11:
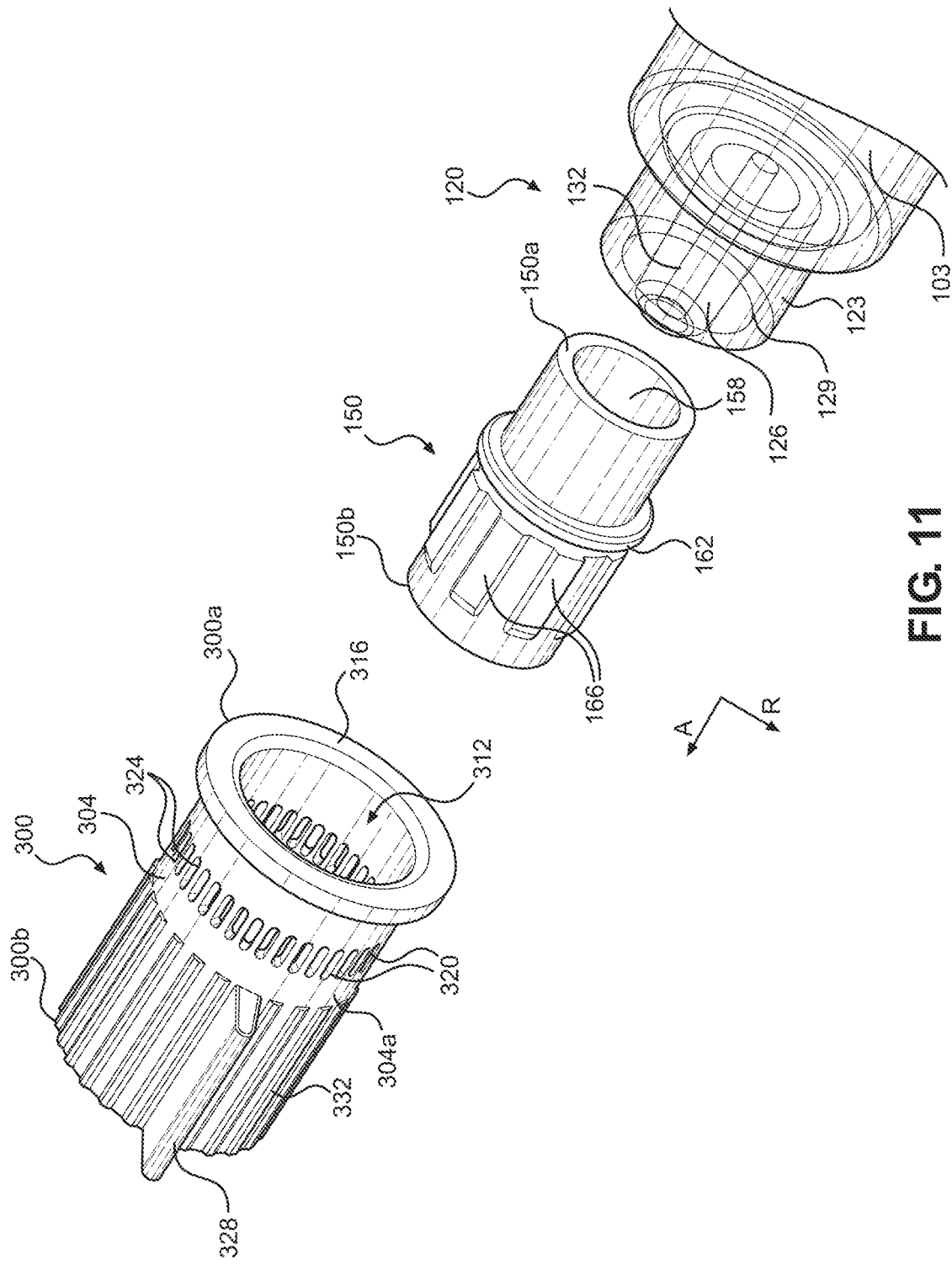
FIG. 11 illustrates an exploded view of a distal portion of the syringe assembly shown in FIG. 10.
Figure 13:
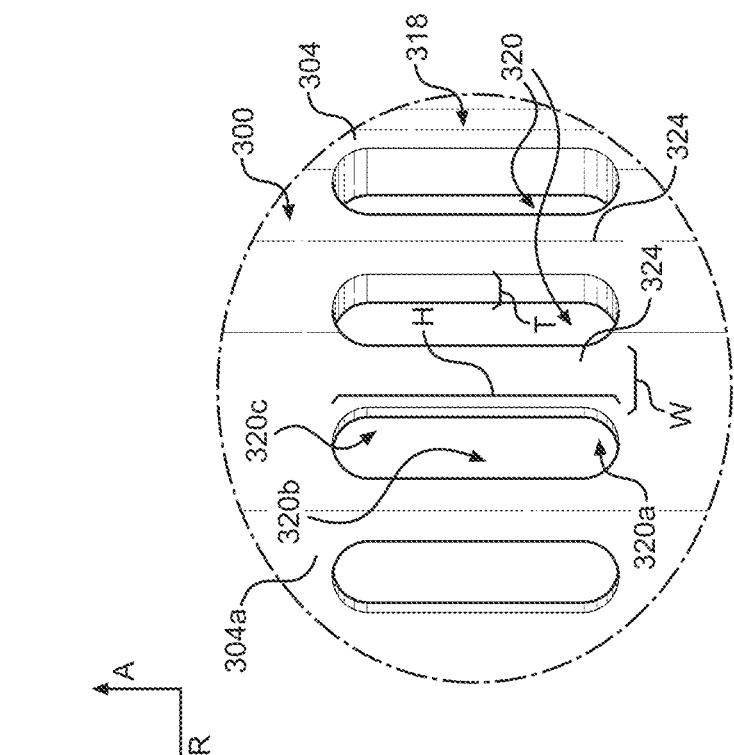
FIG. 13 illustrates an expanded view of the encircled portion of the tamper evident cap shown in FIG. 12.
Figure 12:
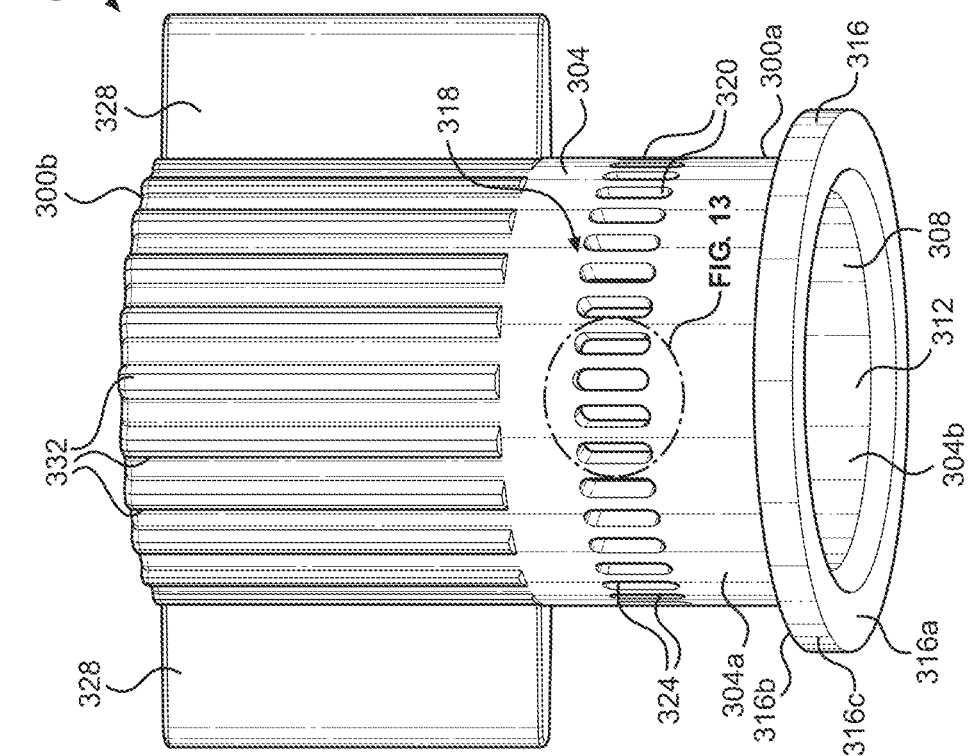
FIG. 12 illustrates a side view of a tamper evident cap of the syringe assembly shown in FIG. 10.
Figure 14:
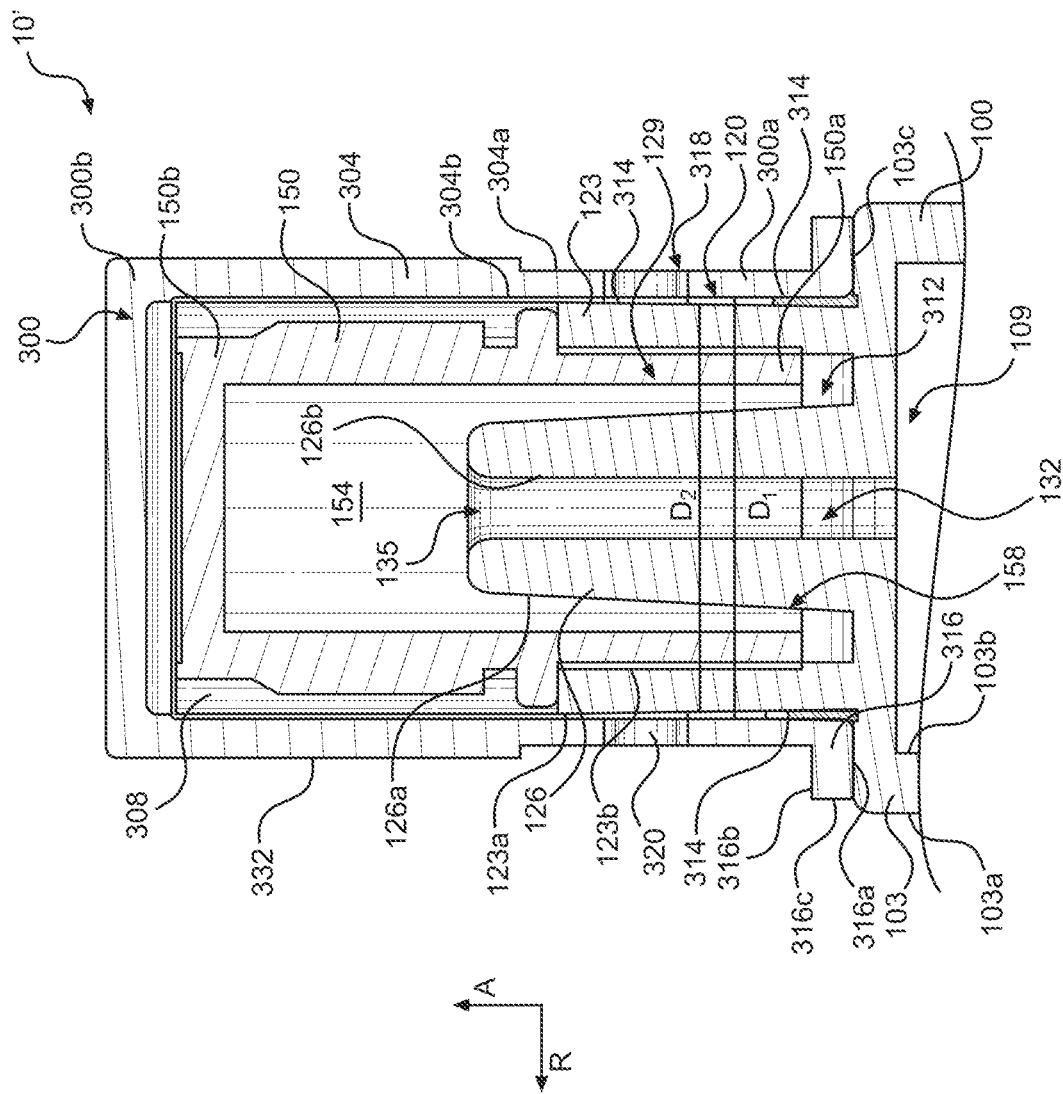
FIG. 14 illustrates a cross-sectional view of a distal portion of the syringe assembly shown in FIG. 10, taken along line 10-10 shown in FIG. 10.

Now referring to FIGS. 1, 8, and 9, the syringe assembly 10 can include a film 244 disposed over portions of the syringe assembly 10. The film 244 can define a substantially continuous, solid body and extend from a proximal end 244a to a distal end 244b opposite the proximal end 244a along the axial direction A. In the depicted embodiment, the proximal end 244a of the film 244 can be disposed around a portion of the barrel body 103 of the syringe 100, while the distal end 244b of the film 244 can be disposed around a portion of the tamper evident cap 200. Specifically, the distal end 244b of the film 244 can be disposed around the proximal end 200a of the tamper evident cap 200 to further secure the tamper evident cap 200 to the Luer connection 120. In certain embodiments, the film 244 may extend on the syringe 100 for a length equal or more than 5 mm, e.g., 10 mm, 15 mm, 20 mm, 30 mm, or more, as measured from the distal end 100b of the syringe 100. Alternatively, or additionally, the film 244 may extend onto the syringe 100 for a length equal to or more than 10%, e.g., 20%, 40%, 60%, or more of the length of the syringe barrel body 103. In certain embodiments, the film 244 may extend on the tamper evident cap 200 for a length equal to or more than 2 mm, e.g., 3 mm, 4 mm, 5 mm, 6 mm, or more, as measured from the proximal end 200a. Alternatively, or additionally, the film 244 may extend onto the tamper evident cap 200 for a length equal to or more than 10%, e.g., 20%, 40%, 60%, or more of the length of the tamper evident cap 200. In other embodiments, the film 244 is continuous through at least a distal portion of the syringe 100 and the entire proximal end 200a of the main body 204 of the tamper evident cap 200. In certain embodiments, the film 244 does not extend over the frangible connection 218 or the distal end 200b of the main body 204 of the tamper evident cap 200.

The film 244 can be blank, or the film 244 can be printed or written on so as to display information related to the type of the material contained within the chamber 109 of the syringe 100. Examples of the type of information that can be printed on the film 244 includes the material's chemical name, generic name, proprietary name, concentration, total volumetric content within the syringe 100, manufacturer, lot number, date of manufacture, and expiration date. The film 244 can also be bar coded with any combination of this information. The film 244 can be fully transparent, partially transparent, or substantially opaque.

In some embodiments, the film 244 is a heat-shrinkable film made of a thermoplastic material selected from the group consisting of polyvinyl chloride (PVC), ethylene vinyl acetate (EVA), polyethylene terephthalate (PET), oriented polystyrene (OPS), oriented polypropylene (OPP), polylactic acid (PLA) and mixtures thereof. In certain embodiments, the film 244 is made of PVC. In certain embodiments, the interior surface of the film 244 or a portion thereof further comprises an adhesive material, such as a glue or a heat-activated adhesive. In certain embodiments, the interior surface of the distal end 244b of the film 244 can be disposed around a portion of the tamper evident cap 200 comprising an adhesive material.

The film 244 can also include a color-coded portion 248 that is indicative of the type of material contained within the chamber 109 of the syringe 100. This allows the user of the syringe assembly 10 to easily determine what material is within the syringe 100 and helps avoid incorrect medicaments from being mistakenly applied to a patient. In one embodiment, the color-coded portion 248 can comprise a substantially solid band positioned near the distal end 244b of the film 244 and extending circumferentially around the film 244. However, alternative placements, shapes, and sizes of the color-coded portion 248 are contemplated. Examples of syringe assemblies 10 having films 244 with various colored color-coded portions 248, 248', 248'', 248''', 248'''' are shown in FIG. 9. The color-coded portion 248 can comprise a color selected from a plurality of colors that each correspond to a different material. The relationship between the color of the color-coded portion 248 and the material contained within the syringe 100 can conform to the labeling standards set by ASTM D4774, such that the color-coded portion 248 can be universally recognized and understood within any variety of medical environments. The standards set by ASTM D4774 are shown in the below table. The examples provided for each drug class are exemplary only and not meant to be exhaustive. Drugs that do not fit into the classes shown in Table 1 can be labeled with black printing on a white background under ASTM D4774 standards. Exceptions are noted by the "A" superscript.

TABLE 1

| ASTM D4774 Standards | | |
| --- | --- | --- |
| Drug Class | Examples | Pantone Color |
| Induction Agents | Etomidate, Ketamine, Methohexital, Propofol, Thiamylal, Thiopental | Yellow |
| Benzodiazepines | Diazepam, Midazolam | Orange 151 |
| Benodiazepine Receptor Antagonist | Flumazenil | Orange 151 and White Diagonal Stripes |
| Muscle Relaxants (Depolarizer) | Succinylcholine[A] | Fluorescent Red 805 |
| Muscle Relaxants (Non Depolarizer) | Atracurium, Cisatracurium, Mivacurium, Pancuronium, Rocuronium, Vecuronium | Fluorescent Red 805 |
| Relaxant Antagonist (Non-Depolarizer) | Endophonium, Neostigmine, Pyridostigmine | Fluorescent Red 805 and White Diagonal Stripes |
| Narcotics | Alfentanil, Fentanyl, Hydromorphone, Meperidine, Morphine, Sufentanil, Remifentanil | Blue 297 |
| Narcotic Antagonists | Levallorphan, Naloxone | Blue 297 and White Diagonal Stripes |
| Vasopressors | Ephedrine, Norepinephrine, Phenylephrine, Epinephrine[A] | Violet 256 |
| Hypotensive Agents | Hydralazine, Nitroglycerine, Nitroprusside, Phentolamine, Trimethaphan | Violet 256 and White Diagonal Stripes |
| Local Anesthetics | Bupivacaine, Chloroprocaine, Lidocaine, Mepivacaine, Procaine, Ropivacaine, Tetracaine | Gray 401 |
| Anticholinergic Agents | Atropine, Glycopyrrolate, Scopolamine | Green 367 |
| Beta Blockers | Esmolol, Labetalol, Metroprolol | White Background with Copper 876U Bar Across Drug Name |
| Major Tranquilizers and Anti-Emetics | Droperidol, Inapsine, Haloperidol, Levomepromazine, Metoclopramide, Ondasetron | Salmon 156 |

[A]Printed against the background color as reversed plate letters with a black bar running from edge to edge of the film Though the film 244 is described as including a color-coded portion 248, it is also contemplated that in other embodiments all or a portion of the main body 204 of the tamper evident cap 200 defines a color-coded portion that is indicative of the type of material within the chamber 109 of the syringe 100 in combination with or in place of the color-coded portion 248. Like the color-coded portion 248, the color-coded portion of the tamper evident cap 200 can comprise a color selected from a plurality of colors that each correspond to a different material. This can be done through molding the color-coded portion of the tamper evident cap 200 out of a different material or a differently colored variety of the same material as the rest of the tamper evident cap 200. In one embodiment, the collar 216 of the tamper evident cap 200 can define the color-coded portion, though other sections of the tamper evident cap 200 can define the color-coded portion as desired. Like the color-coded portion 248, the color coded portion of the tamper evident cap 200 can conform to the labeling standards set by ASTM D4774.

As stated above, the proximal end 244a of the film 244 can be disposed around a portion of the barrel body 103 of the syringe 100, while the distal end 244b of the film 244 can be disposed around a portion of the tamper evident cap 200. The film 244 can be fitted over the tamper evident cap 200 and the syringe 100 such that the film 244 is configured to secure the proximal end 200a of the tamper evident cap 200 to the syringe 100 when the frangible connection 218 breaks. In particular, the external ribs 228 on the proximal end 200a can engage the film 244 so as to ensure that the film 244 retains the proximal end 200a attached to the syringe 100. In one embodiment, this engagement is formed by shrink-wrapping the film 244 over the proximal end 200a of the tamper evident cap 200 and at least a portion of the syringe 100. In other embodiments, the film 244 is adhesive-bonded to the proximal end 200a of the tamper evident cap 200 and at least a portion of the barrel body 103. In yet other embodiments, the film 244 is secured to the proximal end 200a of the tamper evident cap 200 and at least a portion of the barrel body 103 by a combination of shrink-wrapping and adhesive-bonding. In addition to the above-described methods of attaching the film 244 to the tamper evident cap 200 and the syringe 100, various other methods of attaching the film 244 may be utilized as desired.

In certain embodiments, the assembly further comprises a label (not shown) which is attached to at least a portion of the barrel body 103 of the syringe 100. The label can be blank, or the label can be printed or written on so as to display information related to the type of the material contained within the chamber 109 of the syringe 100. Examples of the type of information that can be printed on the label includes the material's chemical name, generic name, proprietary name, concentration, total volumetric content within the syringe 100, manufacturer, lot number, date of manufacture, and expiration date. The label can also be bar coded with any combination of this information. The label can be colored or partially colored, and the label can be fully transparent, partially transparent, or substantially opaque. The label can be comprised of paper, a heat-shrinkable material, an adhesive, or any other suitable materials. In some embodiments, the label is imprisoned between at least a portion of the film 244 and the syringe 100.

Now referring to FIGS. 10-14, another embodiment of a syringe assembly 10' will be discussed in detail, where the syringe assembly 10' includes an alternative embodiment of a tamper evident cap 300. The syringe assembly 10' can include a plunger rod 25, plunger 50, and syringe 100 that are substantially similar to that of the syringe assembly 10. As such, these components will not be described again here for brevity. The tamper evident cap 300 can include a main body 304 that extends from a proximal end 300a to a distal end 300b along the axial direction A. The main body 304 can be configured as a substantially hollow cylinder, though other shapes are contemplated, as the shape of the tamper evident cap 300 can vary according to the shape of the syringe 100, and specifically the Luer connection 120. Like the tamper evident cap 200, the tamper evident cap 300 can be formed through injection molding, and can comprise a plastic such as medical grade polypropylene, polycarbonate, or polyethylene terephthalate. However, other methods of forming the tamper evident cap 300 and other materials for forming the tamper evident cap 300 are contemplated. The main body 304 defines an outer surface 304a and an inner surface 304b opposite the outer surface 304a, where the inner surface 304b defines a passage 308 configured to receive the Luer connection 120 and the tip cap 150. The distal end 300b of the main body 304 can be closed, opened, or partially closed, whereas the proximal end 300a can define an opening 312, where the passage 308 extends from the opening 312 along the axial direction A and terminates within the main body 304 at a location proximal to the distal end 300b. The inner surface 304b of the main body 304, and thus the passage 308, can define a first diameter $D_1$ that extends along the radial direction R, while the outer surface 123a of the outer wall 123 of the Luer connection 120 can define a second diameter $D_2$ that extends along the radial direction R, where the second diameter $D_2$ can be larger than the first diameter $D_1$. The reasoning for this diameter discrepancy will be discussed further below.

In operation, the tamper evident cap 300 can be attached to the syringe 100 by pressing the tamper evident cap 300 over the Luer connection 120 and the tip cap 150 via a force applied along the axial direction A. When this occurs, the inner surface 304b of the main body 304 of the tamper evident cap 300 will form an interference fit with the Luer connection 120, specifically the outer surface 123a of the outer wall 123 of the Luer connection 120. This interference fit can cause the tamper evident cap 300, and particularly the proximal end 300a, to resist being disengaged from the Luer connection 120 as a result of a distally or rotationally applied force. Due to the difference between the first and second diameters $D_1$, $D_2$, the main body 304 may be forced to bend outwards as it is disposed over the Luer connection 120, which can strengthen the interference fit. Further, in one embodiment, to strengthen the interference fit a gripping material 314 may be attached to the inner surface 304b of the main body 304 at the proximal end 300a. The gripping material 314, which can be an adhesive or rubber, can engage the Luer connection 120 and thus aid in preventing relative rotation or axial movement between the proximal end 300a of the main body 304 and the syringe 100. However, it is contemplated that the tamper evident cap 300 can be devoid of any gripping material 314. Additionally, in other embodiments the proximal end 300a of the main body 304 can be attached to the Luer connection 120 via a sonic weld. In certain embodiments, the tamper evident cap 300 is further secured to the Luer connection 120 by a film 244 as discussed hereinabove.

When the tamper evident cap 300 is attached to the Luer connection 120, the tamper evident cap 300 can be spaced in an entirety from the tip cap 150, such that a gap is formed between the tamper evident cap 300 and the tip cap 150 and no portion of the tamper evident cap 300 contacts the tip cap 150. This lack of engagement between the tamper evident cap 300 and the tip cap 150 allows the tamper evident cap 300 to be used simply with existing syringe 100 and tip cap 150 assemblies without interfering with the seal the tip cap 150 creates with the Luer connection 120. Other tamper evident cap designs can require complete redesign of the syringe and/or tip cap, which requires additional tooling for manufacture, thus increasing total manufacturing cost and complexity. The tamper evident cap 300 of the present application presents none of these difficulties. Additionally, this spacing prevents the distal end 300b of the tamper evident cap 300 from being reattached to the syringe assembly 10' after the frangible connection 318 between the proximal and distal ends 300a, 300b has broken, as will be discussed below.

The tamper evident cap 300 can also include a ridge 316 that extends radially outwards from the proximal end 300a of the main body 304. The ridge 316 can have a proximal surface 316a, a distal surface 316b opposite the proximal surface 316a along the axial direction A, and a side surface 316c that extends from the proximal surface 316a to the distal surface 316b. Though depicted as a substantially annular disc, it is contemplated that the ridge 316 can define other shapes as desired. When the tamper evident cap 300 is engaged with the Luer connection 120, the proximal surface 316a of the ridge 316 can abut the distal surface 103c of the barrel body 103 of the syringe 100 so as to limit the axial movement of the tamper evident cap 300 and indicate to the user of the syringe assembly 10' that the tamper evident cap 300 is fully in place. Notably, the diameter of the ridge 316 may not extend out past the diameter of the outer surface 103a of the barrel body 103, and as well as not extend proximally past the distal surface 103c. As a result, the ridge 316 can be spaced in an entirety from the outer surface 103a of the barrel body 103. Because of this, a user of the syringe assembly 10' maintains a complete line of sight with the material within the chamber 109 of the syringe 100, thus allowing the user to be constantly aware of the amount of material within the syringe 100. The ridge 316 does not prevent the user from viewing any portion of the material within the chamber 109.

Continuing with FIGS. 10-14, the tamper evident cap 300 can include a frangible connection 318 positioned axially between the proximal and distal ends 300a, 300b of the main body 304. The frangible connection 318 is configured to be the portion of the tamper evident cap 300 that enables the tamper evident cap 300 to indicate to a user whether the syringe assembly 10' has been tampered with. When the tamper evident cap 300 is attached to the Luer connection 120, the frangible connection 318 is configured to break under a force applied to the distal end 300b of the main body 304. The force can be a clockwise or counter-clockwise rotational force, though other forces are contemplated. As a result, the distal end 300b will be decoupled from the proximal end 300a, and the proximal end 300a of the main body 304 will remain attached to the Luer connection 120 of the syringe 100 when the frangible connection 318 breaks. The frangible connection 318 is thus designed such that the force required to break the frangible connection 318 is less than the force required to decouple the proximal end 300a from the Luer connection 120. If a user of the syringe assembly 10' sees that the frangible connection 318 of the tamper evident cap 300 is broken, the user knows that the material within the chamber 109 of the syringe 100 may have been tampered with. However, if the frangible connection 318 is intact, the user can be assured of a greatly reduced risk that the material has been tampered with.

The frangible connection 318 comprises a plurality of frangible bridges 324 positioned circumferentially around the main body 304. The frangible bridges 324 can extend around an entirety of the circumference of the main body 304, such that when the frangible connection 318 breaks, the distal end 300b of the main body 304 can be completely separated from the proximal end 300a. Each of the frangible bridges 324 can comprise a thin, elongate portion of the main body 304 having a height H measured along the axial direction A, a width W measured along the circumference of the main body 304, and a thickness T measured along the radial direction R. The thickness T of the frangible bridges 324 can be consistent with the thickness of the rest of the main body 304, though it is contemplated that the frangible bridges 324 may be thinner than the rest of the main body 304 so as to promote easier breaking. Also, the frangible bridges 324 can be equidistantly spaced about the circumference of the main body 304. Though the frangible bridges 324 are shown as having a specific design and spacing, it is contemplated that the frangible bridges 324 can be differently sized or spaced as desired.

The frangible connection 318 can also define a plurality of gaps 320 that extend through the main body 304 from the outer surface 304a to the inner surface 304b, where a gap 320 can be extend circumferentially between two frangible bridges 324. As depicted, each of the gaps 320 includes a central elongate section 320b between first and second semi-circular end portions 320a, 320c. As such, each of the gaps 320 can take the form of a substantially oval passage through the main body 304, though other embodiments are contemplated. Though each of the gaps 320 is shown as being identical, each of the gaps 320 can vary in design and spacing along with the design and spacing of each frangible bridge 324. The inclusion of the frangible bridges 324 and gaps 320 allows the tamper evident cap 300 to be easily broken at the frangible connection 318.

Distal to the frangible connection 318, the tamper evident cap 300 can include wings 328 that extend outwards from the outer surface 304a of the main body 304 along the radial direction R. The wings 328 can extend such that each defines the radially outward-most point on the tamper evident cap 300, allowing the wings 328 to easily be grasped by a user so as to allow the user to twist the tamper evident cap 300 to break the frangible connection 318. In the depicted embodiment, the tamper evident cap 300 includes two wings 328 extending from the outer surface 304a at opposed locations on the main body 304. However, the tamper evident cap 300 can include more or less wings 328 as desired. For example, the tamper evident cap 300 can include one, three, four, or more than four wings 328.

Additionally, the tamper evident cap 300 can include ribs 332 that extend outwards from the outer surface 304a of the main body 304 along the radial direction R. Compared to the wings 328, the ribs 332 can extend to a much smaller extent from the main body 304, and can function as texturing for the user to easily grasp the main body 304 and break the frangible connection 318. In the depicted embodiment, the tamper evident cap 300 includes a plurality of ribs 332 extending from the outer surface 304a and arranged circumferentially between the wings 328. Though the tamper evident cap 300 is shown as including a certain number and design of ribs 332, the ribs 332 can be differently configured as desired.

Figure 15B:
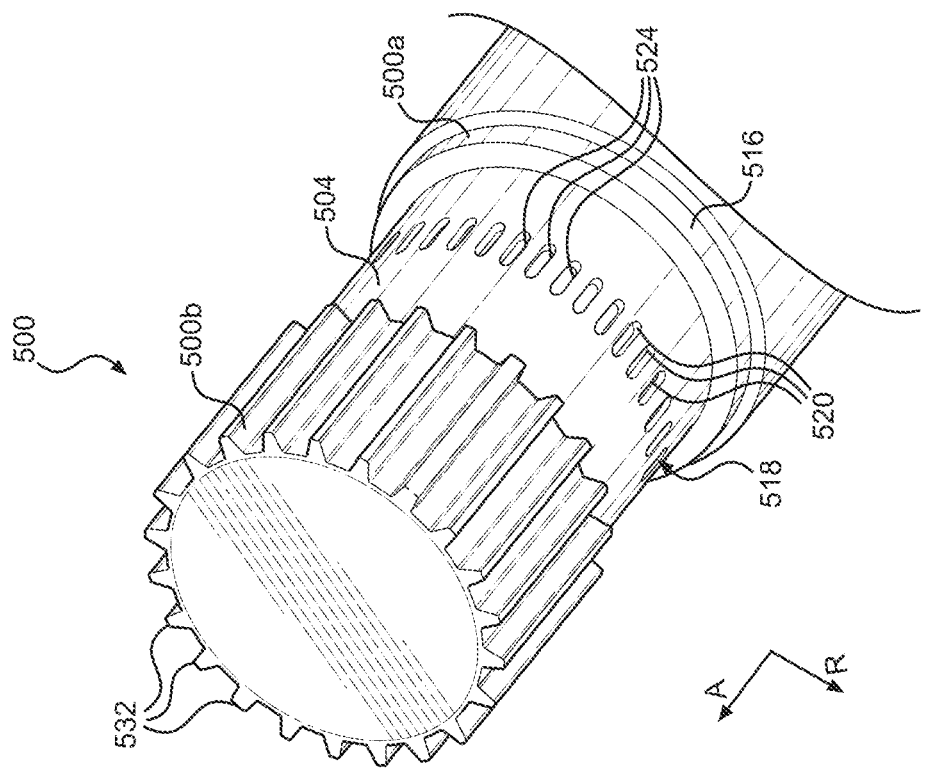
FIG. 15B illustrates a perspective view of a distal portion of a tamper evident cap according to another embodiment of the present disclosure.
Figure 15A:
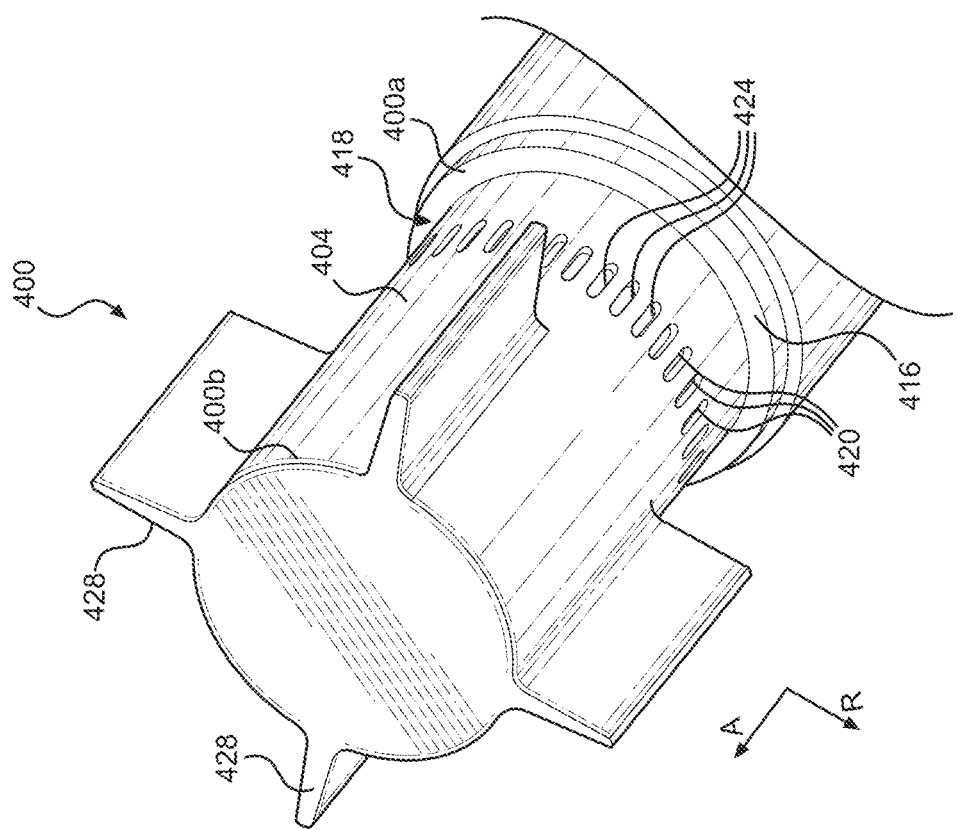
FIG. 15A illustrates a perspective view of a tamper evident cap according to another embodiment of the present disclosure.

Now referring to FIG. 15A, a tamper evident cap 400 according to another embodiment of the present disclosure is shown. The tamper evident cap 400 has a main body 404 that extends from a proximal end 400a to a distal end 400b opposite the proximal end 400a along the axial direction A. The tamper evident cap 400 can also define a ridge 416 extending radially outwards from the proximal end 400a of the main body 404. The tamper evident cap 400 can also have a frangible connection 418 positioned between the proximal end 400a and the distal end 400b. When the tamper evident cap 400 is attached to the Luer connection 120, the frangible connection 418 is configured to break under a force applied to the distal end 400b of the main body 404. As a result, the distal end 400b will be decoupled from the proximal end 400a, and the proximal end 400a of the main body 404 will remain attached to the Luer connection 120. Like the frangible connection 318, the frangible connection 418 can be comprised of a plurality of gaps 420 and frangible bridges 424 arranged circumferentially around the main body 404. Unlike the tamper evident cap 300, the tamper evident cap 400 can include only wings 428 that extend outwards from the outer surface of the main body 404 along the radial direction R. The tamper evident cap 400 includes four wings 428 and no ridges, where the wings 428 are equidistantly spaced around the circumference of the main body 404 (each wing 428 is spaced from the adjacent wings 428 by 90 degrees). Like the wings 328, the wings 428 allow for a user to more easily grasp the tamper evident cap 400 and apply a force to the distal end 400b of the tamper evident cap 400.

Referring to FIG. 15B, a tamper evident cap 500 according to another embodiment of the present disclosure is shown. The tamper evident cap 500 has a main body 504 that extends from a proximal end 500a to a distal end 500b opposite the proximal end 500a along the axial direction A. The tamper evident cap 500 can also define a ridge 516 extending radially outwards from the proximal end 500a of the main body 504. The tamper evident cap 500 can also have a frangible connection 518 positioned between the proximal end 500a and the distal end 500b. When the tamper evident cap 500 is attached to the Luer connection 120, the frangible connection 518 is configured to break under a force applied to the distal end 500b of the main body 504. As a result, the distal end 500b will be decoupled from the proximal end 500a, and the proximal end 500a of the main body 504 will remain attached to the Luer connection 120. Like the frangible connection 318, the frangible connection 518 can be comprised of a plurality of gaps 520 and frangible bridges 524 arranged circumferentially around the main body 504. Unlike the tamper evident cap 300, the tamper evident cap 500 can include no wings and only ribs 532 that extend outwards from the outer surface of the main body 504 along the radial direction R. The tamper evident cap 500 can include a plurality of ribs 532 arranged around a substantial entirety of the circumference of the main body 504. Like the ribs 332, the ribs 532 allow a user to easily grasp the main body 504 and more easily apply a force to the distal end 500b of the tamper evident cap 500.

As discussed herein, a tamper evident cap according to the present invention can have a plurality of ribs, wings or other protrusions that extend outwards from the outer surface of the main body. In some embodiments, the pattern and/or texture of the protrusions can be indicative of the type of material contained within the chamber of the syringe. This allows the user of the syringe assembly to easily determine what material is within the syringe and helps avoid incorrect medicaments from being mistakenly applied to a patient.

Another embodiment of the present disclosure is a pharmaceutical product comprising a syringe assembly 10, 10' and a secondary packaging system therefor. In some embodiments, the secondary packaging is a pouch, blister, flow wrapper, or bag. The secondary packaging can be comprised of an oxygen, light, and/or moisture barrier material, such as high density polyethylene (HDPE), ethylene/vinyl alcohol copolymer (EVOH), polypropylene (PP), polyethylene terephthalate (PET), polyethylene naphthalate (PEN), and polyamide (PA), metalized film, aluminum foil, oxide coated films, and combinations thereof. In certain embodiments, the secondary packaging system also comprises an oxygen absorber. The oxygen absorber can be a sachet, pouch, canister, capsule, sticker, or strip that is placed inside of the secondary packaging. Alternatively, or additionally, the oxygen absorber can be incorporated into the material of the secondary packaging. In some embodiments, the oxygen absorber is selected from the group consisting of reduced iron compounds, catechol, ascorbic acid and analogs thereof, metal ligands, unsaturated hydrocarbons and polyamides.

Yet another embodiment of the present disclosure is a pharmaceutical product comprising a plurality of syringe assemblies 10, 10' and a container therefor. In some embodiments, the container is a box, carton, case, package, tray, or tin. Optionally, one or more of the syringe assemblies 10, 10' can be enclosed within a secondary packaging system before being placed into the container. In certain embodiments, each syringe assembly 10, 10' enclosed within the container is filled with the same active ingredient. In other embodiments, each syringe assembly 10, 10' enclosed within the container is filled with a different active ingredient from the same drug class, a different active ingredient from a different drug class, or any combination thereof. For example, the pharmaceutical product can comprise a plurality of syringe assemblies 10, 10' enclosed with a container, wherein the two or more of the syringe assemblies 10, 10' are filled with a different active ingredient from a first drug class, and one or more syringe assemblies 10, 10' are filled with an active ingredient from a second drug class.

Figure 16:
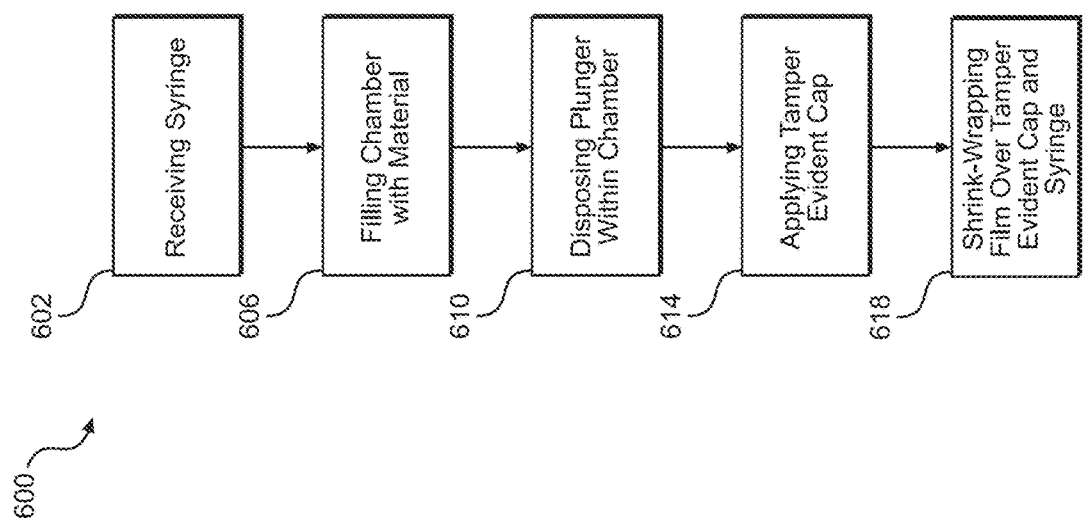
FIG. 16 illustrates a process flow diagram of a method of filling a syringe with a material according to an embodiment of the present disclosure.

Now referring to FIG. 16, a method 600 of filling the syringe 100 with material will be described. Method 600 begins with step 602, which comprises receiving the syringe 100, where the syringe 100 has the barrel body 103 extending from a distal end 100b to an open proximal end 100a. In step 602, the syringe 100 can be received with the tip cap 150 placed over the outlet so as to create a fluid seal over the outlet 135. Then, step 606 comprises filling the chamber 109 with the material through the outlet 135 of the Luer connection 120, where the Luer connection 120 extends along the axial direction A from the barrel body 103. Next, in step 610, the plunger 50 is disposed at the proximal end 100a of the barrel body 103 within the chamber 109. As stated above, the plunger rod 25 is connected to the plunger 50, the plunger rod 25 having a rod body 28 that extends from the proximal end 28a disposed outside the chamber 109 to a distal end 28b disposed within the chamber 109 and connected to the plunger 50. The chamber 109 is defined by the barrel body 103 and extends along the axial direction A, therethrough.

After step 610, step 614 involves applying the tamper evident cap 200, 300, 400, 500 over the Luer connection 120 and the tip cap 150, such that the tamper evident cap 200, 300, 400, 500 is spaced from the tip cap 150. Step 614 can also involve pressing the tamper evident cap 200, 300, 400, 500 over the Luer connection 120 and the tip cap 150 via a force applied along the axial direction A. Step 614 also can include forming an interference fit between the tamper evident cap 200, 300, 400, 500 and the outer surface 123a of the outer wall 123 of the Luer connection. Alternatively, or additionally, step 614 can include engaging a gripping material 314 attached to an inner surface of the tamper evident cap 200, 300, 400, 500 with the Luer connection 120.

In certain embodiments, step 618 can also be performed, which involves shrink-wrapping a film 244 over the proximal end 200a of the tamper evident cap 200 and at least a portion of the syringe 100. As such, through engagement between the film 244 and the syringe 100 and between the film 244 and the tamper evident cap 200, in particular the external ribs 228 of the proximal end 200a, the film 244 can secure the proximal end 200a to the syringe 100. This allows the film 244 to secure the proximal end 200a in engagement with the syringe 100 even after the frangible bridge 224 is broken and the distal end 200b of the tamper evident cap 200 is detached. The film 244 can include a color-coded portion 248 that is indicative of the type of material within the chamber 109 of the syringe 100. The color-coded portion can 248 can comprise a color selected from a plurality of colors that each correspond to a different material. The color of the color-coded portion 248 can correspond to the type of material within the chamber 109 in accordance with ASTM D4774. Step 618 can also include bonding the film 244 to the syringe 100 and/or the tamper evident cap 200.

In another embodiment, as shown in FIG. 17, a method 700 of filling the syringe 100 with material begins with step 702, which comprises receiving the syringe 100, where the barrel body 103 of the syringe 100 extends from a distal end 100b to an open proximal end 100a, and the tip cap 150 placed over the outlet 135 so as to create a fluid seal over the outlet 135. Then, step 704 comprises applying the tamper evident cap 200, 300, 400, 500 over the Luer connection 120 and the tip cap 150 ca before the chamber 109 is filled with material. Then, step 706 comprises filling the chamber 109 with the material through the opening 106 at the proximal end 100a. Next, in step 710, the plunger is disposed at a proximal end of the chamber 109.

In yet another embodiment of the invention, as shown in FIG. 18, a method 800 of applying the tamper evident cap 200, 300, 400, 500 to the syringe 100, which is prefilled, is shown. Method 800 begins with step 802, in which the syringe 100 is received prefilled with a material and including a tip cap 150 placed over the outlet 135. Then, the tamper evident cap 200, 300, 400, 500 is applied over the Luer connection 120 and the tip cap 150 in step 806 as described above in the context of method 600.

The material contained within the chamber 109 of the syringe 100 in the syringe assemblies 10, 10' typically is a liquid, which can be aqueous, non-aqueous, or a combination of aqueous and non-aqueous liquids. In some embodiments, the liquid is a diluent intended for mixing with an active ingredient prior to administration to a subject. Exemplary diluents include, but are not limited to, water, 0.9% saline, 5% dextrose, Ringer's lactate solution, and other pharmaceutically acceptable diluents. In other embodiments, the liquid is a pharmaceutical formulation comprising an active ingredient and, optionally, one or more excipients. Thus, the invention provides a pharmaceutical product comprising a syringe assembly according to the present invention, wherein the liquid is a pharmaceutical formulation. Suitable excipients include, but are not limited to, a tonicity modifier, antioxidant, buffer, pH adjuster, preservative, solubilizer, stabilizer, or a combination of any of the forgoing. A diluent or pharmaceutical formulation can take on any suitable physical form including, but not limited to, solution, suspension, emulsion, or dispersion.

The active ingredient of the pharmaceutical formulation can be a therapeutic agent, a diagnostic agent, a nutrient, or a combination thereof. Examples of therapeutic agents include, but are not limited to antiinfectives, anesthetics, analgesics, anticoagulants, chemotherapeutics, hormones, antihypertensives, antiinflammatories, antiemetics, bronchodilators, adrenergics, immunoglobulins, antipsychotics, antidepressants, and combinations thereof. Examples of diagnostic agents include, but are not limited to x-ray, MRI and ultrasound contrast agents, cholecystokinetics, vasodilators, and combinations thereof. Examples of nutrients include, but are not limited to, salts, carbohydrates, minerals, vitamins, lipids, and combinations thereof.

In some embodiments, the active ingredient is a compound useful for pain management, muscle relaxation, sedation, and/or anesthesia. In certain embodiments, the active ingredient is an opioid, a benzodiazepine, beta blocker, or an $\alpha_2$-adrenergic receptor agonist. In particular embodiments, the active ingredient is morphine, hydromorphone, hydrocodone, oxycodone, oxymorphone, codeine, buprenorphine, naloxone, naltrexone, fentanyl, remifentanil, sufentanil, alfentanil, meperidine, rocuronium, vecuronium, midazolam, lorazepam, diazepam, neostigmine, atropine, glycopyrrolate, dexmedetomidine, cisastracurium, ropivacaine, lidocaine, propofol, ketamine, succinylcholine, or a combination of the foregoing.

In other embodiments, the active ingredient is moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, decitabine, azacitidine, docetaxel, pemetrexed, palonosetron, aprepitant, fosaprepitant, famotidine, amiodarone, nitroglycerin, nicardipine, clevidipine, dobutamine, esmolol, labetalol, metroprolol, somatropin, liraglutide, abaloparatide, semaglutide, teriparatide, degarelix, sumatriptan, epinephrine, ephedrine, vasopressin, methotrexate, testosterone, hydroxyprogesterone, or a combination of the foregoing.

Figure 19:
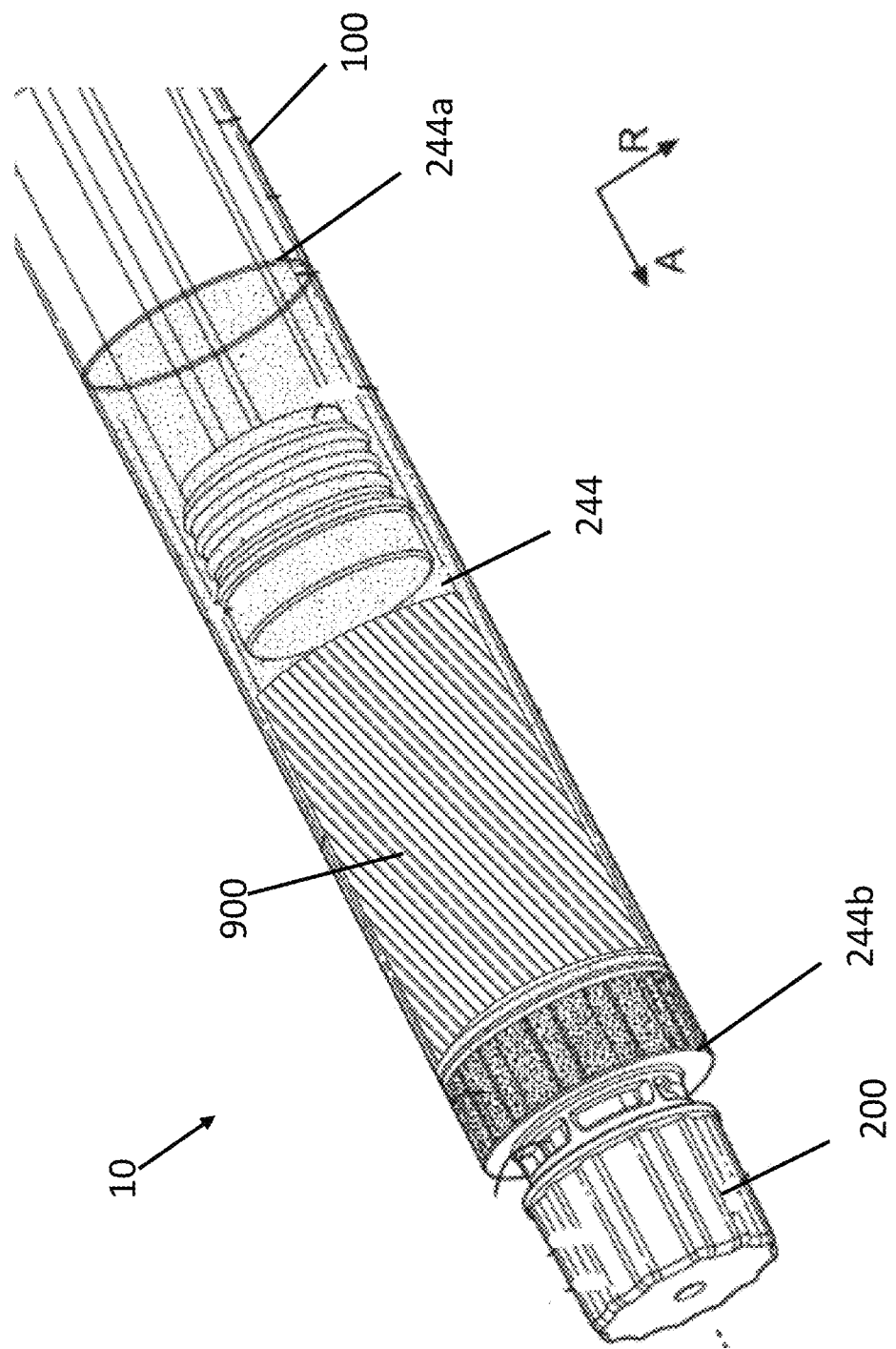
FIG. 19 illustrates a perspective view of a syringe assembly with an RFID tag in accordance with an embodiment of the present disclosure.

In yet another embodiment, as shown in FIG. 19, the syringe 100 can include one or more components for tracking, monitoring, and/or identifying the syringe assembly 10 and/or its contents. In some aspects, the film 244 disposed on the syringe 100 may include a radio frequency identification (RFID) label or tag 900. Signal communication to or from an RFID label is a form of wireless communication that uses radio waves to identify and track objects.

The RFID tag 900 may be configured to be affixed to the film 244 or, alternatively, may be part of a unitary component of the film 244. It will be appreciated that the RFID tag 900 can be utilized with any of the syringe assemblies disclosed throughout this application. The RFID tag 900 should be dimensioned and arranged relative to the syringe 100 such as to not interfere with the described structure or operation of the tamper evident caps 200, 300, 400, or 500 of any of the embodiments disclosed herein. In some aspects, the RFID tag 900 may be affixed to the syringe 100 separate from the film 244. In some aspects, an embodiment with the RFID tag 900 may be devoid of the film 244. In some aspects, the RFID tag 900 may be affixed to the tamper evident cap 200, 300, 400, or 500. In some aspects, the RFID tag 900 may be affixed to both, the syringe 100 and the tamper evident cap 200, 300, 400, or 500.

Figure 20A:
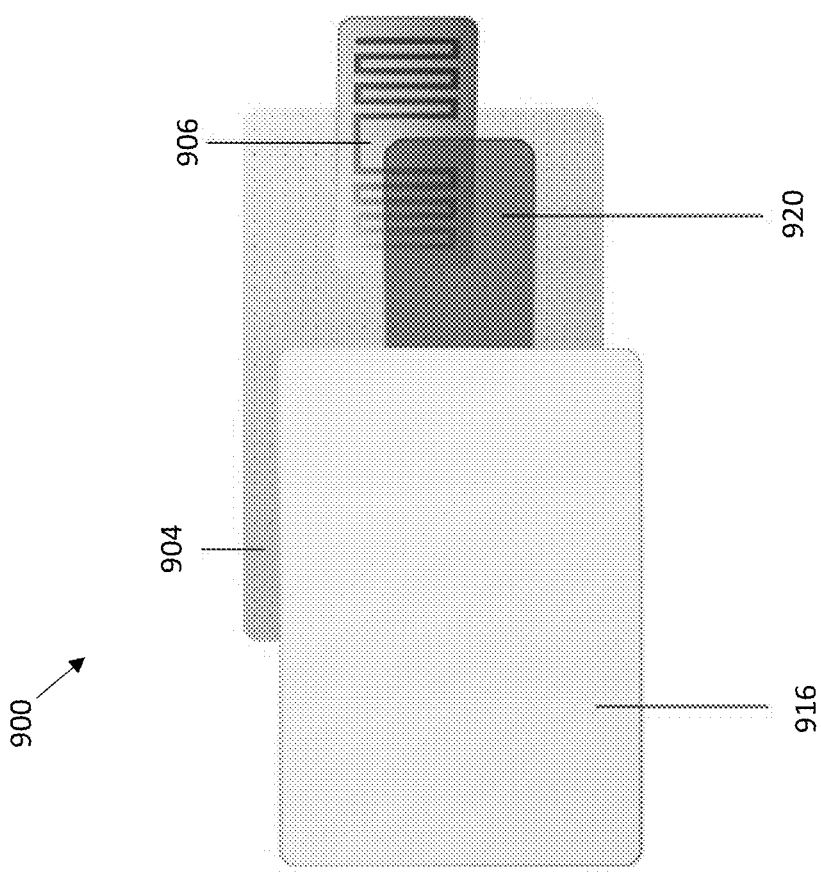
FIG. 20A illustrates an exploded perspective view of an RFID tag in accordance with an embodiment of the present disclosure.

Referring to FIG. 20A, the RFID tag 900 may include a backing 904 configured to be received on the syringe 100. The backing 904 may be secured to the syringe 100 via an adhesive or another suitable fixing mechanism. The backing 904 may include an adhesive thereon or, alternatively, may be configured to receive an adhesive between the syringe 100 and the backing 904. In some aspects, the film 244, as described throughout this application, may comprise the backing 904. The backing 904 may be a separate component of the film 244 or, alternatively, at least a portion of the film 244 may be used as the entire backing 904 of the RFID tag 900.

Figure 21A:
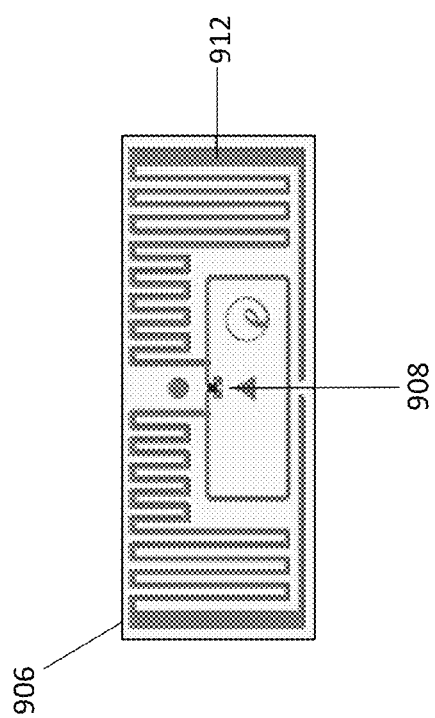
FIG. 21A illustrates a front perspective view of an RFID tag in accordance with an embodiment of the present disclosure.
Figure 21B:
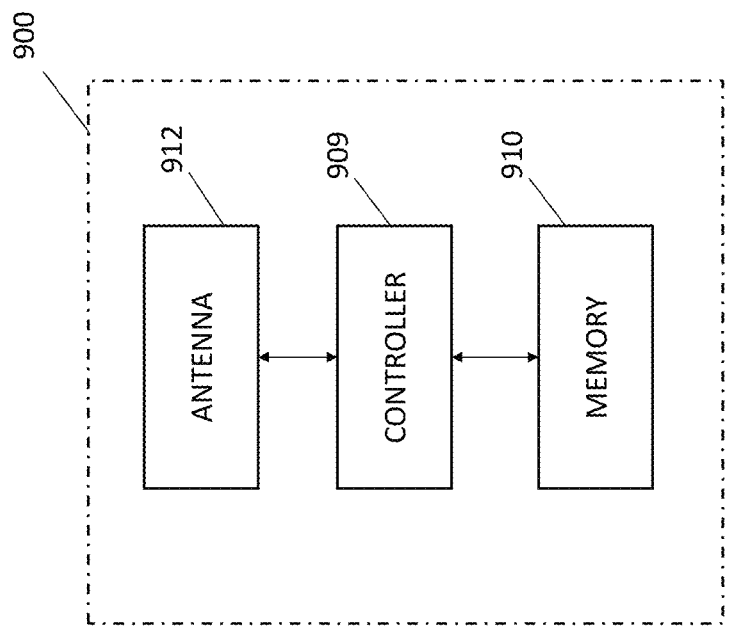
FIG. 21B illustrates a schematic of an RFID tag in accordance with an embodiment of the present disclosure.

The RFID tag 900 further includes an integrated circuit 908 that is connected to an antenna 912. The integrated circuit 908 is configured to store electronic data therein and to communicate with the antenna 912. Referring to FIG. 21B, the integrated circuit 908 may include a controller 909 and a memory 910. The memory 910 may include non-volatile memory and is configured for read/write access to receive, store, and allow access to electronic data transmitted to or from the RFID tag 900. The controller 909 is configured to read the electronic data from the memory 910 and to write electronic data to the memory 910. The controller 909 is configured to cause the antenna 912 to transmit the electronic data from the memory 910 to a reader 930 and to receive electronic data from the antenna 912 into the memory 910, as will be described in detail below. The antenna 912 is configured to communicate with the integrated circuit 908 and to transmit electronic data to and/or from the integrated circuit 908. The antenna 912 may be configured to supply power to the integrated circuit 908 sufficient to actuate the read/write process on the integrated circuit 908 to initiate transmission of the electronic data.

Figure 20B:
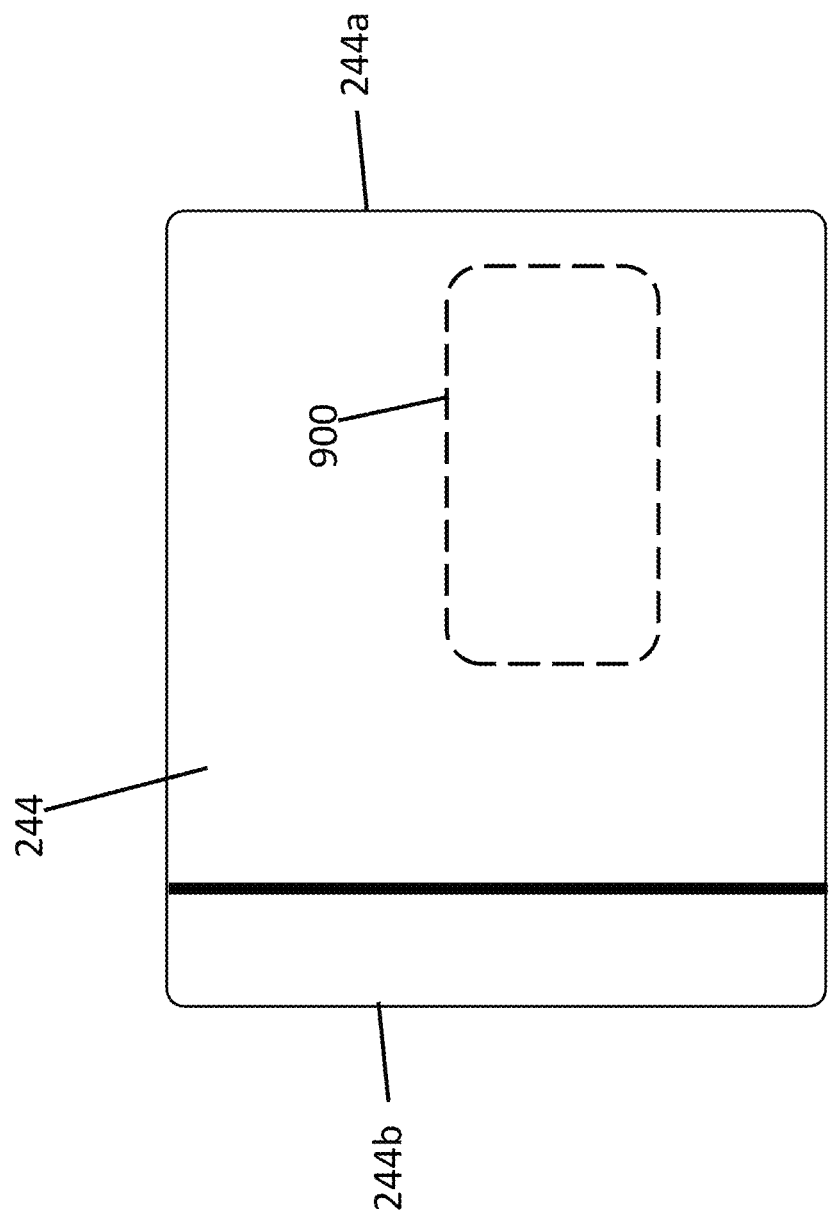
FIG. 20B illustrates a front perspective view of an RFID tag (shown in phantom) covered by a film in accordance with an embodiment of the present disclosure.

The integrated circuit 908 and/or the antenna 912 may be disposed on the backing 904, for example, opposite the syringe 100. In some aspects, the integrated circuit 908 and/or the antenna 912 may be adhered to the backing 904. In some aspects, the integrated circuit 908 and the antenna 912 may be secured relative to the syringe 100 by an external label 916. The external label 916 may be configured to adhere to the backing 904 (or the film 244) such that the integrated circuit 908 and the antenna 912 are held in friction fit between the external label 916 and the backing 904 (or the film 244). In some aspects, the external label 916 may be configured to contact the syringe 100 directly without contacting the backing 904 or the film 244. The external label 916 may include printed text, barcodes, graphics, or other visual identifiers thereon. Exemplary visual identifiers that have been described throughout this application with respect to the film 244 may also apply to the external label 916 and/or to the backing 904. In use, the RFID tag 900 may be hidden from view under the external label 916 or by the film 244 (see FIG. 20B). In some aspects, such as shown in FIGS. 20A and 21A, the integrated circuit 908 and the antenna 912 may be held together on an inlay layer 906. It will be understood that the inlay layer 906 serves to retain the integrated circuit 908 and the antenna 912 and may not be required for any other purpose in the RFID tag 900. With reference to embodiments disclosed throughout this application, in some embodiments, at least a portion of the RFID tag 900 (e.g. the integrated circuit 908 and the antenna 912) may be disposed between the film 244 and the syringe barrel body 103.

In some aspects, an intermediate layer 920 may be disposed between the external label 916 and the integrated circuit 908 and antenna 912. The intermediate layer 920 may provide structural and/or electromagnetic protection to the integrated circuit 908 and the antenna 912. The intermediate layer 920 may be disposed adjacent the inlay layer 906.

In some aspects, the backing 904 may be disposed such that the integrated circuit 908 and the antenna 912 are disposed between the backing 904 and the syringe 100. In such embodiments, the RFID tag 900 may include the additional external label 916 contacting the backing 904 opposite the integrated circuit 908 and the antenna 912, or, alternatively, such embodiments may be devoid of an external label 916 entirely.

Figure 22:
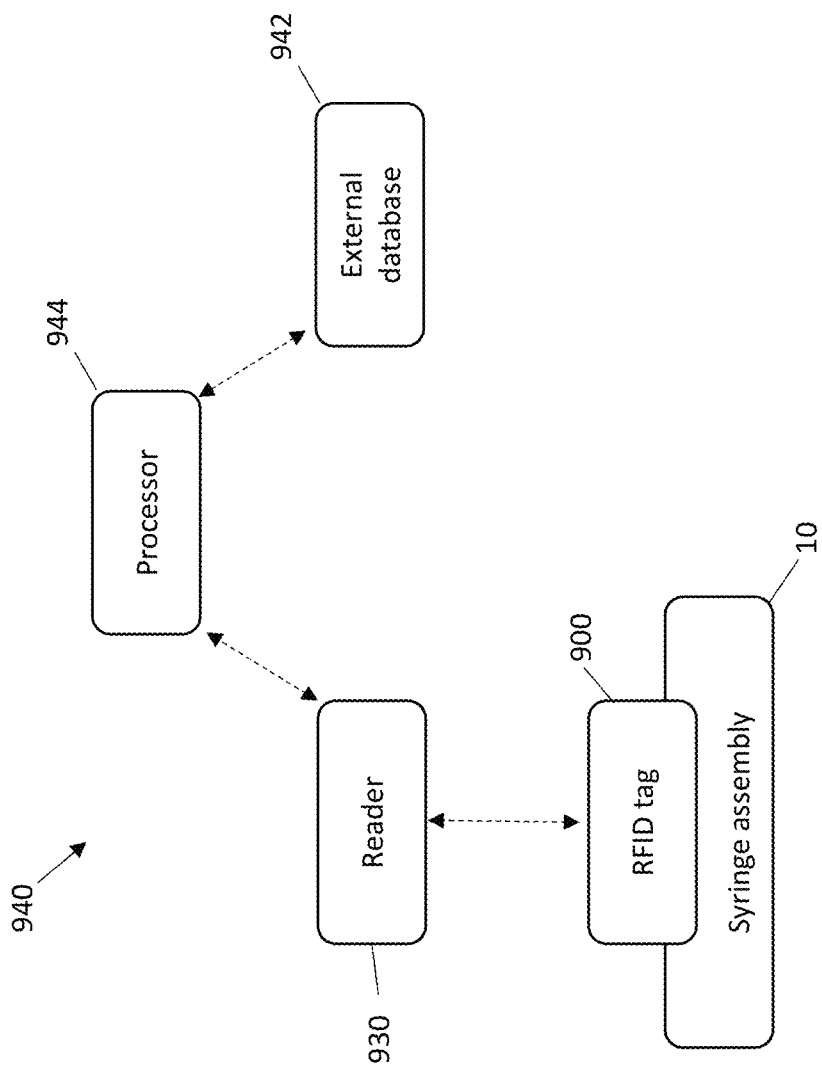
FIG. 22 illustrates a schematic of an RFID network in accordance with an embodiment of the present disclosure.

The RFID tag 900 can be used to track and monitor the syringe assembly to which it is affixed, for example, syringe assemblies 10 and 10' as disclosed throughout this application. The RFID tag 900 can include active or passive RFID technology. In an active RFID system, the RFID tag includes a transmitter and a power source configured to activate the RFID tag and transmitter to broadcast an electronic signal with electronic data. The power source may include a battery or photovoltaic cell. In a passive RFID system, an RFID reader is configured to send a radio signal to the RFID tag. The antenna on the RFID tag can receive the signal and use that signal actuate transmittal of electronic data to/from the integrated circuit. The RFID tag 900 described herein can be designed and configured for either active or passive operation. It will be understood that if the RFID tag 900 is an active RFID tag, a transmitter and power source would need to be operationally connected thereto. In preferred embodiments, as shown in FIG. 22, the RFID tag 900 may be configured to interact with various components of a network 940. The RFID tag 900 can be a passive RFID tag that is configured to receive electronic power from an RFID reader 930. The reader 930 is configured to receive data from the RFID tag 900. Although referred to as a "reader," it will be understood that such a device may be configured to transmit data to the RFID tag 900. As such, the reader 930 may also be described as a writer 930. In some aspects, the reading and writing functionalities can be performed by a single device 930, which will be referred to as the reader 930. The RFID reader 930 is configured to provide the connection between the RFID tag 900 and an external system configured to send and/or receive information to and/or from the RFID tag 900. The external system may include a personal computing device, a network server, or a computing cloud. The RFID reader 930 is configured to communicate with the RFID tag 900 (or with a plurality of RFID tags 900) that are within the read/write range of operation. The RFID reader 930 is configured to perform various tasks, such as simple continuous inventorying, searching for RFID tags 900 that meet predetermined criteria, writing (or encoding) to selected RFID tags 900, or other electronic communications.

The RFID tag 900 can be designed to operate within known frequency ranges for RFID communication systems, including low frequency (LF), high frequency (HF), and ultra-high frequency (UHF). The LF band can cover frequencies from about 30 KHz to about 300 KHz. For RFID purposes, LF devices typically utilize either 125 KHz or 134.2 KHz frequencies. The LF band can be configured to operate within a range of up to approximately 10 cm for reading and/or writing from and/or to the RFID tag 900. The HF band can include frequencies in the range of from about 3 MHz to about 30 MHz and may be configured to operate within a range of up to approximately 100 cm. For RFID purposes, HF devices typically operate at 13.56 MHz. The UHF frequency band can cover frequencies from about 300 MHz to about 3000 MHz and may be configured to operate within a range of up to approximately 1200 cm. For RFID purposes, UHF devices typically operate at a range of between about 860 MHz to about 960 MHz (for passive RFID) and at about 433 MHZ (for active RFID). In some embodiments, the RFID tag 900 can be configured to operate at a frequency within the UHF spectrum although it will be appreciated that this disclosure is not limited to any particular frequency range.

The RFID tag 900 can receive, store, transmit, and/or otherwise make available information that is electronically stored therein, for example in the integrated circuit 908. With continued reference to FIG. 22, the reader 930 can further communicate with a processor 944 that is configured to communicate with data in a database 942 to provide instructions to the reader 930 to receive data from the RFID tag 900 or send data to the RFID tag 900, as well as to process the received data based on predetermined instructions. The RFID tag 900 can include various information, including at least a product identifier, product serial number, lot number, expiration date, or a combination of any of the above. The information can be sent to or received from the RFID tag 900 via the reader 930. In some embodiments, the RFID tag 900 can include at least all four of the product identifier, serial number, lot number, and expiration date. The serial number may be unique and may pertain to the individual syringe assembly or component thereof or, alternatively, to a particular type of assembly or medicament therein. The product identifier can refer to a graphical or alpha-numeric string of characters that represents the particular products to which the RFID tag 900 is attributed, for example, a syringe assembly 10 or a medicament within the syringe assembly 10. The product identifier may include a Global Trade Item Number (GTIN). The GTIN is an identifier for trade items that can be referenced within, or compared to, a database. In aspects where the RFID tag 900 is intended to correspond to a medicament, the GTIN may include a National Drug Code (NDC) that corresponds to a particular medicament or medicament component, such as a specific pharmaceutical compound. The particular NDC associated with a respective RFID tag 900 can be included in the NDC Directory maintained by the United States Food and Drug Administration (FDA). It will be appreciated that the GTIN may include a drug code that is different from the NDC, for example one that corresponds to a drug code directory outside of the United States. The RFID tag 900 may be designed to comply with one or more national or international standards for labeling, such as GSI and/or ISO. The RFID tag 900 may include the same information stored electronically within the integrated circuit 908 and appearing visually on the backing 904 or the external label 916.

In some aspects, the RFID tag 900 may receive some or all of the information detailed above at substantially the same time or, alternatively, may receive data over a plurality of write cycles, in which the data is electronically transmitted from the reader 930 to the RFID tag 900. In some aspects, the RFID tag 900 may be pre-encoded with the product identifier information and with the serial number prior to being applied to a syringe assembly, such as any of the assemblies described throughout this application. The RFID tag 900 may receive additional data, such as the lot number and expiration date, at a later time. In some aspects, some or all of the electronic data provided on the RFID tag 900 may be modified by the reader 930.

Figure 23:
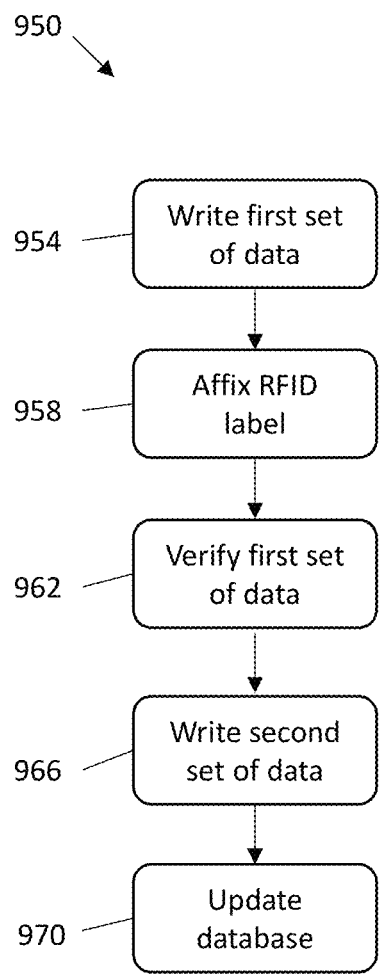
FIG. 23 illustrates a flow chart of a method of labeling a syringe assembly in accordance with an embodiment of this disclosure.

An exemplary encoding process 950 is depicted in FIG. 23. It will be appreciated that the RFID tag 900 may be encoded in a different process and that some of the steps described in the process 950 may be omitted, repeated, or changed in order relative to other steps. Referring to step 954, the RFID tag 900 is placed in electronic communication with the reader 930, and the reader 930 electronically transmits a first set of data to the RFID tag 900. The first set of data may include the product identifier and/or the serial number. The first set of data may be associated with a database 942 stored on the reader 930 or stored on an external computing device, server, network, or cloud and accessible by the reader 930. The database 942 is configured to communicate with the reader 930 via a processor 944. The processor 944 may be disposed on or in the reader 930 or on a separate computing device. The processor 944 and the database 942 may be disposed on the same device or on different devices. The processor 944 is configured to electronically communicate with the database 942 and with the reader 930. The electronic communication may be wired or wireless. The reader 930 is configured to transmit the signal to the antenna 912 of the RFID tag 900. The controller 909 in the integrated circuit 908 is configured to receive the signal from the antenna 912, encode or decode the signal according to preprogrammed instructions to generate storable data associated with the signal, and move the data associated with the signal to the memory 910 in the integrated circuit 908.

In step 958, the RFID tag 900 is then be applied to the syringe assembly 10, 10', or another embodiment disclosed herein. The RFID tag 900 can be applied to the syringe 100 as described above. In some aspects, this step may be performed prior to step 954, such that the RFID tag 900 is affixed to the syringe 100 prior to the first set of data being transmitted to the RFID tag 900. Alternatively, this step may be performed later in the process 950, for example after the step 962 described below.

In step 962, the reader 930 is configured to be placed in electronic connection with the RFID tag 900 such that data can be transmitted between the RFID tag 900 and the reader 930. The reader 930 receives data that is stored on the RFID tag 900, for example the first set of data that may include the product identifier and/or the serial number that was transmitted to the RFID tag 900 in step 954. The controller 909 accesses the data stored on the memory 910, performed any necessary encoding or decoding step according to preprogrammed instructions, and sends the data to the reader 930 through the antenna 912. The reader 930 communicates the received information with a processor 944 configured to relate the received information with predetermined instructions, such as with a threshold, algorithm, or other computer programmed instruction. The processor 944 is configured to compare the received information per the predetermined instructions to determine if the information meets predetermined criteria. The comparison may be done with a predetermined set of data (for example a "control" set of data). In some aspects, the received set of data may include the first set of data that was transmitted to the RFID tag 900 in step 954, and the control set of data may include the same information as the first set of data. The comparison step may include determining if the received set of data matches the control set of data. If the information meets the criteria (e.g. if the received set of data matches the control set of data), the RFID tag 900 (and the assembly to which the RFID tag 900 is affixed) is considered to be "verified," and the process can continue to the next step. If the information received by the reader 930 in this step does not meet the predetermined criteria, the RFID tag 900 and the related assembly are not verified, and additional checking or verification steps may be performed. For example, if the RFID tag 900 is not verified, this could mean that the RFID tag 900 is damaged or improperly affixed to the syringe 100, in which case the RFID tag 900 may be replaced. In some aspects, lack of verification could mean that the first set of data transmitted to the RFID tag 900 in step 954 was not successful, in which case, step 954 may be repeated. In some aspects, the RFID tag 900 may have been tampered with, in which case the RFID tag 900 and/or any other component of the syringe assembly may be fixed or replaced.

In step 966, the reader 930 is configured to be placed in electronic connection with the RFID tag 900 (or remain in electronic connection with the RFID tag 900. The reader 930 is configured to transmit a second set of data to the RFID tag 900. The second set of data may include the lot number and/or the expiration date of the product or assembly. In some aspects, step 966 may be performed a plurality of times to transmit individual portions of data separately, for example, performed a first time to transmit the lot number to the RFID tag 900 and performed a second time to transmit the expiration date. It will be appreciated that additional information may be electronically transmitted to, and stored in, the integrated circuit 908 of the RFID tag 900.

In step 970, the reader 930 and/or the connected processor 944 may update a database with information pertaining to the RFID tag 900 processed in steps 954 to 966, for example to update inventory.

In some aspects, an additional step of printing visual indicators on the RFID tag 900 may be conducted. Although visual information does not affect the electronic reading or writing to the RFID tag 900, visual information may provide a level of redundancy to ensure that the necessary information appears on the label.

By using radio waves to encode the RFID tags 900 and then read information from those RFID tags 900, a user can track and monitor inventory without a visual line of sight. Because RFID readers 930 can receive electronic data from a plurality of RFID tags 900 simultaneously, less time can be spent on verifying individual tags (as would need to be done if utilizing a different tracking technique, such as visual inspection or barcode scanning). Information related to the RFID tags 900 can be stored in the database 942 and can be easily accessed. In some aspects, the database 942 may be configured to be updated automatically when information received by the reader 930 is different from the information stored in the database 942 with respect to the particular RFID tag 900 (i.e. with respect to the particular product identifier or serial number assigned to the RFID tag 900 or the syringe assembly). This allows for real-time updating of the database when a product with an RFID tag 900 is accessed, moved, or tampered with. In some aspects, a plurality of products may be disposed within a storage container, such as a cabinet. As the product is placed into the storage container, the reader 930 receives information related to the product, and the database 942 is updated to account for that product. If the product is removed from the storage container, the reader 930 no longer receives information related to that product and its affixed RFID tag 900. The database 942 may be updated to account for removal of that product.

By relying on RFID technology, inventory can be monitored and tracked more easily to ensure sufficient amount of desired products. Similarly, by monitoring expiration date, the inventory can be adjusted to remove expired products and ensure unexpired products are maintained at the desired quantities. Digitally monitoring and storing inventory information can also reduce information loss that often accompanies manual record keeping. Furthermore, as the process can be automated for all products, individual user approach differences are eliminated to increase precision in inventory management. Additionally, time spent on inventorying, locating expired products, and locating recalled lots is decreased. Using RFID technology further allows for immediate updating of the inventory when a product is removed and reduces chances of human error, such as when a user forgets to update inventory upon adding or removing a product. Additionally, monitoring how each tagged product or assembly is used, how often, how much, and in which circumstances can help users determine future inventory needs and/or efficacy of treatments. Information written to the RFID tag 900 can be validated through cGMP to ensure high quality and accuracy.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts, and features of the inventions—such as alternative materials, structures, configurations, methods, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features, and concepts may be expressly identified herein as being inventive or forming part of an invention, such identification is not intended to be exclusive, but rather there may be inventive aspects, concepts, and features that are fully described herein without being expressly identified as such or as part of a specific invention, the scope of the inventions instead being set forth in the appended claims or the claims of related or continuing applications. Descriptions of exemplary methods or processes are not limited to inclusion of all steps as being required in all cases, nor is the order that the steps are presented to be construed as required or necessary unless expressly so stated.

While the invention is described herein using a limited number of embodiments, these specific embodiments are not intended to limit the scope of the invention as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in a particular order as desired.

What is claimed is:

1. A syringe assembly, comprising:
   a syringe having a barrel body that extends from a proximal end to a distal end and defines a chamber extending along an axial direction therethrough, and a Luer connection extending from the distal end along the axial direction and defining an outlet in fluid communication with the chamber, wherein the chamber contains a material;

a plunger received within the chamber of the syringe to create a fluid seal within the barrel body;

a tip cap defining a central passage configured to receive a portion of the Luer connection such that the tip cap creates a fluid seal over the outlet;

a tamper evident cap disposed over the Luer connection, the tamper evident cap having a main body that defines a proximal end defining an opening, a distal wall opposite the proximal end along the axial direction, an outer surface, and an inner surface opposite the outer surface that defines a passage configured to receive the tip cap and the Luer connection, wherein the tamper evident cap is spaced from the tip cap, the main body further defining a frangible connection between the proximal and distal ends of the main body; and a radio-frequency identification (RFID) tag disposed on the syringe and configured to receive and store data related to the syringe assembly, wherein the RFID tag includes an integrated circuit, configured to store electronic information thereon, and an antenna operatively connected to the integrated circuit and configured to receive a signal from an RFID reader to cause transmission of at least part of the electronic information from the integrated circuit, and wherein the frangible connection is configured to break under a force applied to the distal end of the tamper evident cap such that the proximal end of the tamper evident cap is configured to remain engaged with the syringe when the frangible connection breaks.

2. The syringe assembly of claim 1, wherein the distal wall of the tamper evident cap closes a distal end of the tamper evident cap.

3. The syringe assembly of claim 1, wherein the distal wall of the tamper evident cap partially closes a distal end of the tamper evident cap.

4. The syringe assembly of claim 1, further comprising:
a film shrink-wrapped over the proximal end of the tamper evident cap and at least a portion of the syringe, wherein the film includes the RFID tag.

5. The syringe assembly of claim 4, wherein the film includes a color-coded portion that comprises a color selected from a plurality of colors that each correspond to a different material.

6. The syringe assembly of claim 5, wherein the color of the color-coded portion corresponds to the material in accordance with ASTM $D_{4774}$.

7. The syringe assembly of claim 4, wherein the film is adhesive-bonded to the tamper evident cap.

8. The syringe assembly of claim 4, wherein the film is adhesive-bonded to the syringe.

9. The syringe assembly of claim 4, wherein the proximal end of the main body includes a plurality of external ribs extending radially outwards from the outer surface and configured to secure the film to the tamper evident cap.

10. The syringe assembly of claim 1, wherein the proximal end of the main body includes a plurality of internal ribs extending radially inwards from the inner surface and configured to form an interference fit with the Luer connection.

11. The syringe assembly of claim 1, wherein the frangible connection comprises a plurality of frangible bridges positioned circumferentially around the main body.

12. The syringe assembly of claim 1, wherein the fluid seal over the outlet is not compromised when the tamper evident cap is disposed over the Luer connection or when the frangible connection is broken.

13. The syringe assembly of claim 1, wherein the RFID tag is a passive RFID tag and is configured to receive an electronic signal from the RFID reader to initiate transmission of the at least part of the electronic information.

14. The syringe assembly of claim 1, wherein the RFID tag is configured to operate at a frequency between 300 MHz and 3000 MHz.

15. The syringe assembly of claim 1, wherein the electronic information includes at least one of a product identifier, a serial number, a lot number, or an expiration date.

16. The syringe assembly of claim 1, wherein the material includes an active ingredient selected from a group consisting of an opioid, benzodiazepine, α2-adrenergic receptor agonist, beta blocker, morphine, hydromorphone, hydrocodone, oxycodone, oxymorphone, codeine, buprenorphine, naloxone, naltrexone, fentanyl, remifentanil, sufentanil, alfentanil, meperidine, rocuronium, vecuronium, midazolam, lorazepam, diazepam, neostigmine, atropine, glycopyrrolate, dexmedetomidine, cisastracurium, ropivacaine, lidocaine, propofol, ketamine, succinylcholine, moxifloxacin, linezolid, levofloxacin, levetiracetam, vancomycin, cefepime, aztreonam, cefoxitin, ceftriaxone, cefazolin, cefotaxime, ceftazidime, gentamicin, oxacillin, nafcillin, penicillin, cefuroxime, ticarcillin, clavulanic acid, piperacillin, tazobactam, azithromycin, meropenem, ertapenem, tigecycline, micafungin, metronidazole, fluconazole, itraconazole, posaconazole, heparin, enoxaparin, dalteparin, theophylline, acetaminophen (paracetamol), ibuprofen, acetylcysteine, decitabine, azacitidine, docetaxel, pemetrexed, palonosetron, aprepitant, fosaprepitant, famotidine, amiodarone, nitroglycerin, nicardipine, clevidipine, dobutamine, esmolol, labetalol, metroprolol, somatropin, liraglutide, abaloparatide, semaglutide, teriparatide, degarelix, sumatriptan, epinephrine, ephedrine, vasopressin, methotrexate, testosterone, and hydroxyprogesterone.

17. A method of labeling a syringe assembly, the method comprising:
providing a label configured to be affixed to a syringe, the label including a radio-frequency identification (RFID) tag, the RFID tag further having an integrated circuit and an antenna operatively connected to the integrated circuit;

transmitting a first set of data to the RFID tag and storing the first set of data in a memory of the integrated circuit of the RFID tag;

verifying the first set of data on the RFID tag; and transmitting a second set of data to the RFID tag and storing the second set of data in the integrated circuit, the second set of data being different from the first set of data.

18. The method of claim 17, wherein the label is placed in electronic connection with an RFID reader, and the first set of data and the second set of data are electronically transmitted by sending a first and second signal, respectively, from the RFID reader to the RFID tag.

19. The method of claim 18, wherein verifying the first set of data comprises receiving the first set of data from the RFID tag by the RFID reader and performing a comparison of the received first set of data with a control set of data.

20. The method of claim 17, wherein transmitting the first set of data includes transmitting a product identifier and a serial number to the RFID tag, and transmitting the second set of data includes transmitting a lot number and an expiration date to the RFID tag.

21. The method of claim 17, further comprising affixing the label to the syringe after the step of transmitting the first set of data but before the step of transmitting the second set of data.

* * * * *